United States Patent
Aharoni

(10) Patent No.: US 9,358,102 B2
(45) Date of Patent: Jun. 7, 2016

(54) METHOD AND APPARATUS FOR PREPARATION AND INSERTION OF AN INTRAOCULAR LENS INTO THE EYE OF A PATIENT

(71) Applicant: VISIONCARE OPHTHALMIC TECHNOLOGIES INC., Saratoga, CA (US)

(72) Inventor: Eli Aharoni, Tel Aviv (IL)

(73) Assignee: Visioncare Ophthalmic Technologies Inc., Saratoga, CA (US)

( * ) Notice: Subject to any disclaimer, the term of this patent is extended or adjusted under 35 U.S.C. 154(b) by 117 days.

(21) Appl. No.: 14/070,958

(22) Filed: Nov. 4, 2013

(65) Prior Publication Data

US 2015/0127014 A1    May 7, 2015

(51) Int. Cl.
   *A61F 2/16*   (2006.01)
   *A61F 9/00*   (2006.01)

(52) U.S. Cl.
   CPC ............. *A61F 2/1662* (2013.01); *A61F 2/1664* (2013.01); *A61F 2/1691* (2013.01); *A61F 9/0017* (2013.01)

(58) Field of Classification Search
   CPC ............... A61F 9/0026; A61F 2209/00865; A61F 2/16; A61F 2/1662; A61F 2/1664; A61F 2/1678; A61F 2202/1681; A61F 2002/1683; A61F 9/0008; A61F 9/0017; A61F 9/0061; A61F 2002/1686; A61F 2002/169; A61F 2002/16902; A61F 2002/19603
   See application file for complete search history.

(56) References Cited

U.S. PATENT DOCUMENTS

| | | | | |
|---|---|---|---|---|
| 4,041,552 A | * | 8/1977 | Ganias | A61F 2/16 623/6.51 |
| 4,136,406 A | * | 1/1979 | Norris | A61F 9/0061 606/107 |
| 4,190,049 A | * | 2/1980 | Hager | A61B 17/30 606/107 |
| 4,214,585 A | * | 7/1980 | Bailey, Jr. | A61F 2/16 606/107 |
| 4,657,547 A | * | 4/1987 | Maggi | A61F 2/16 623/6.53 |
| 4,662,882 A | * | 5/1987 | Hoffer | A61F 2/16 623/6.55 |
| 4,750,904 A | * | 6/1988 | Price, Jr. | A61F 2/16 623/6.51 |
| 5,336,262 A | * | 8/1994 | Chu | A61F 2/16 128/898 |
| 5,480,426 A | * | 1/1996 | Chu | A61F 2/16 656/6.55 |

(Continued)

*Primary Examiner* — Jonathan W Miles
*Assistant Examiner* — Kankindi Rwego
(74) *Attorney, Agent, or Firm* — Fish & Richardson P.C.

(57) ABSTRACT

A method for insertion of an intraocular lens into the eye of a patient, the method including removably attaching loop extensions to loops of an intraocular lens prior to insertion of the intraocular lens into the eye of a patient, initially inserting into the eye of the patient the loop extensions, pulling on the loop extensions through sclerectomies formed in the sclera of the eye of the patient, inserting the intraocular lens into the eye of the patient, positioning the intraocular lens in a desired position in the eye of the patient by pulling on the loop extensions through the sclerectomies, and fixing the loops to the sclera of the eye of the patient at the sclerectomies and detaching the loop extensions from the loops.

21 Claims, 26 Drawing Sheets

(56) References Cited

U.S. PATENT DOCUMENTS

| | | | | |
|---|---|---|---|---|
| 5,814,103 A * | 9/1998 | Lipshitz | A61F 2/1648 623/6.34 |
| 6,152,959 A * | 11/2000 | Portney | A61F 2/1602 623/6.38 |
| 6,193,750 B1 * | 2/2001 | Cumming | A61F 2/1613 623/6.11 |
| 6,352,542 B1 * | 3/2002 | Snyder | A61B 17/0482 606/148 |
| 7,175,661 B1 * | 2/2007 | Chung | A61F 2/1602 623/6.41 |
| 2004/0111152 A1 * | 6/2004 | Kelman | A61F 2/1629 623/6.37 |
| 2007/0027541 A1 * | 2/2007 | Aharoni | A61F 2/1613 623/6.41 |
| 2013/0238091 A1 * | 9/2013 | Danta | A61F 2/1613 623/6.43 |
| 2014/0371852 A1 * | 12/2014 | Aharoni | A61F 2/15 623/6.51 |

* cited by examiner

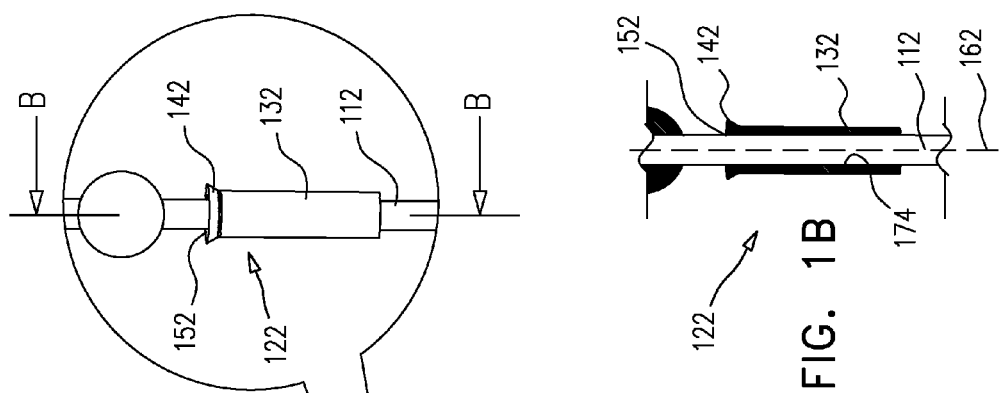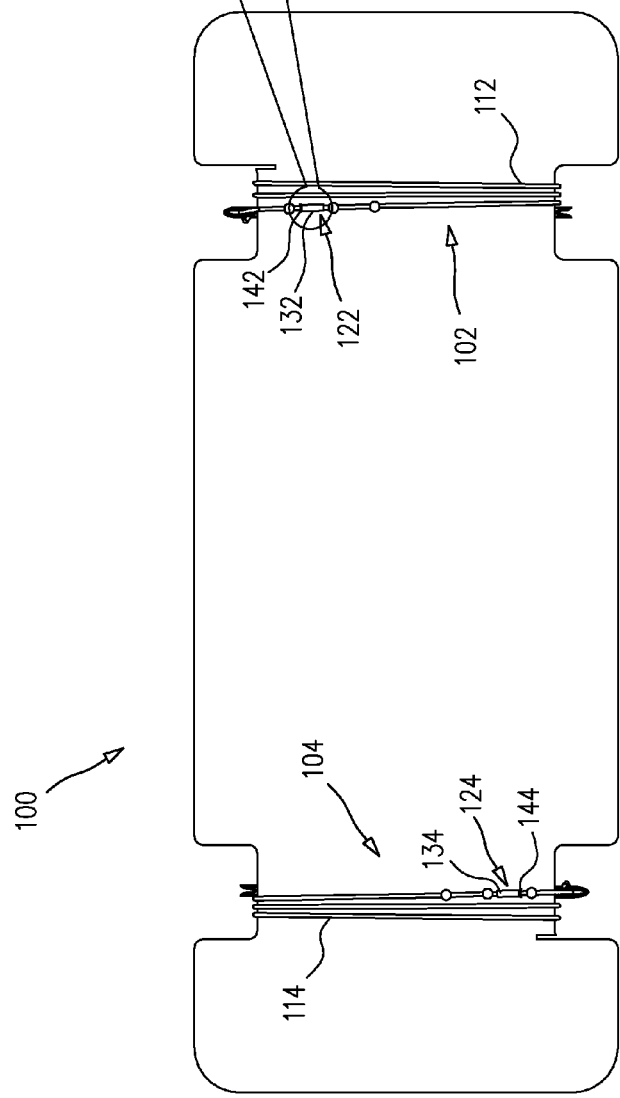

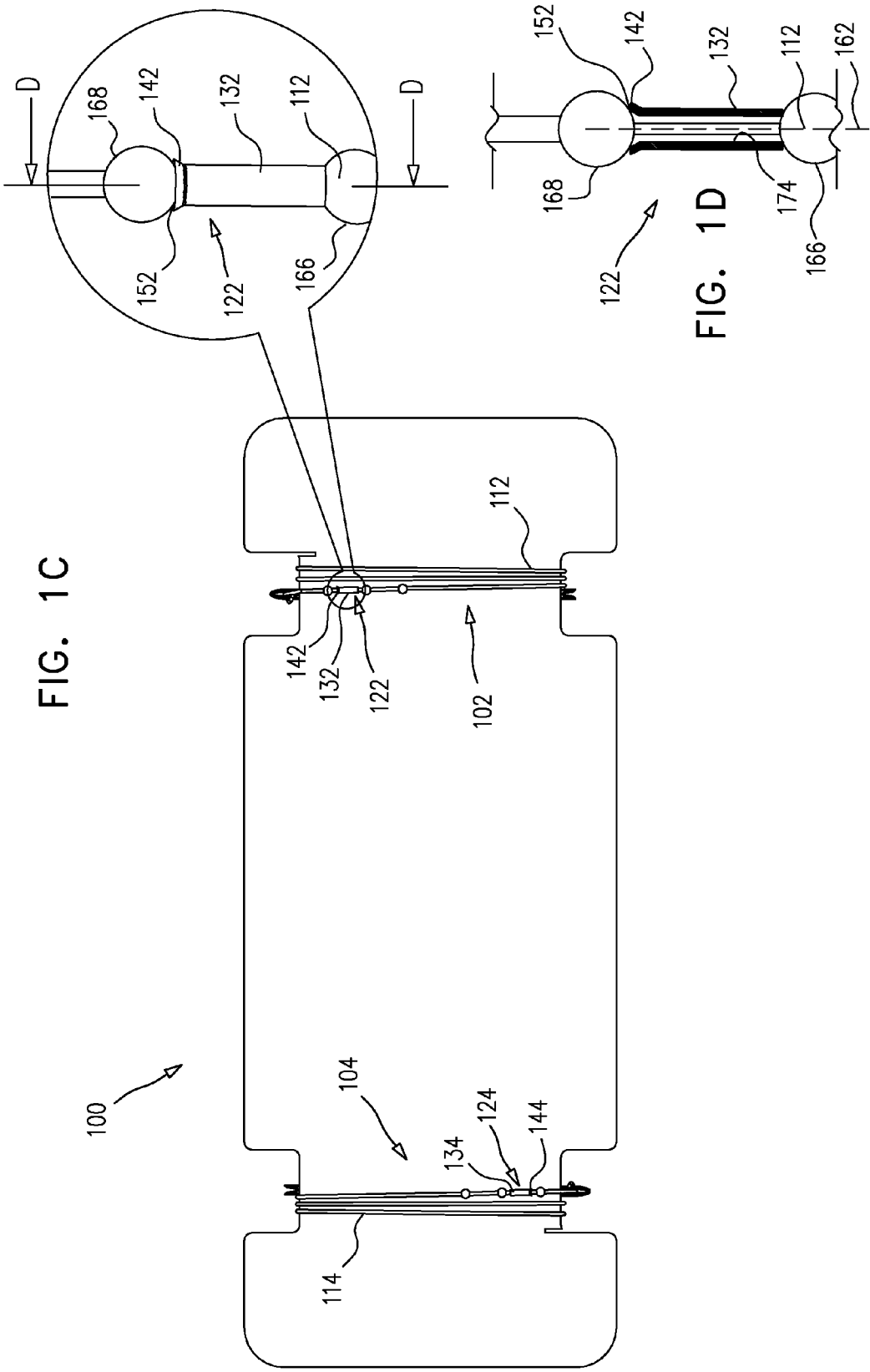

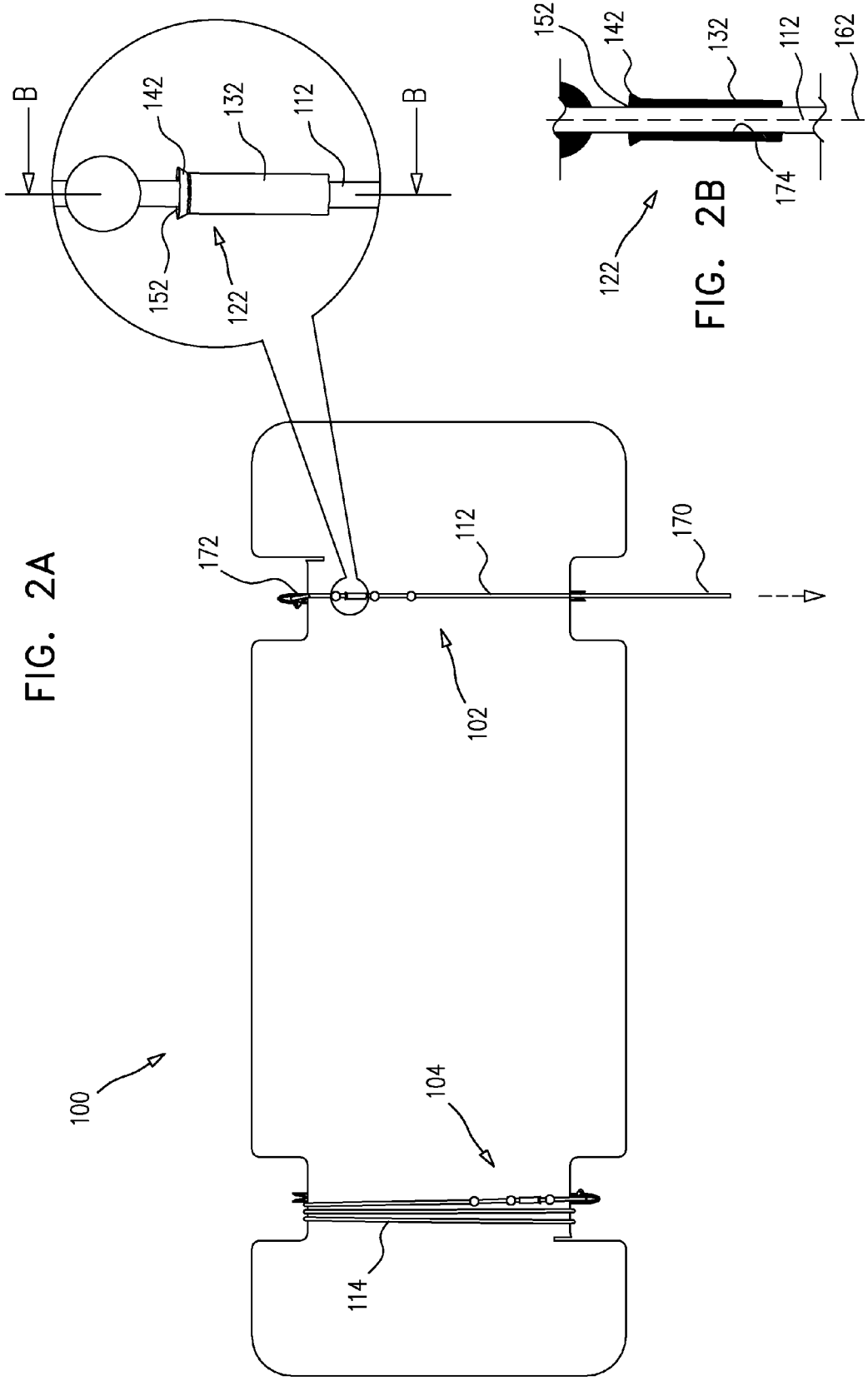

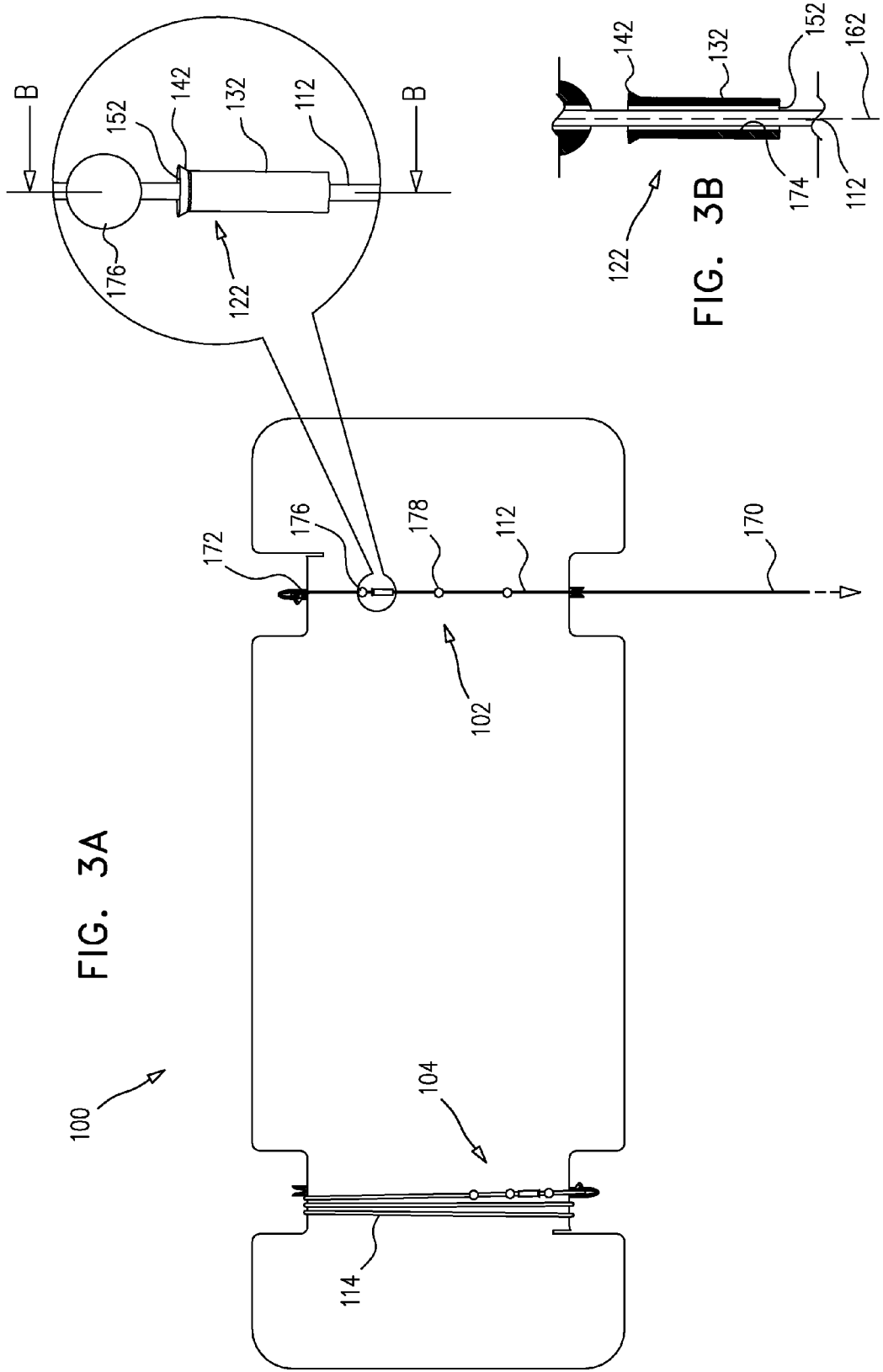

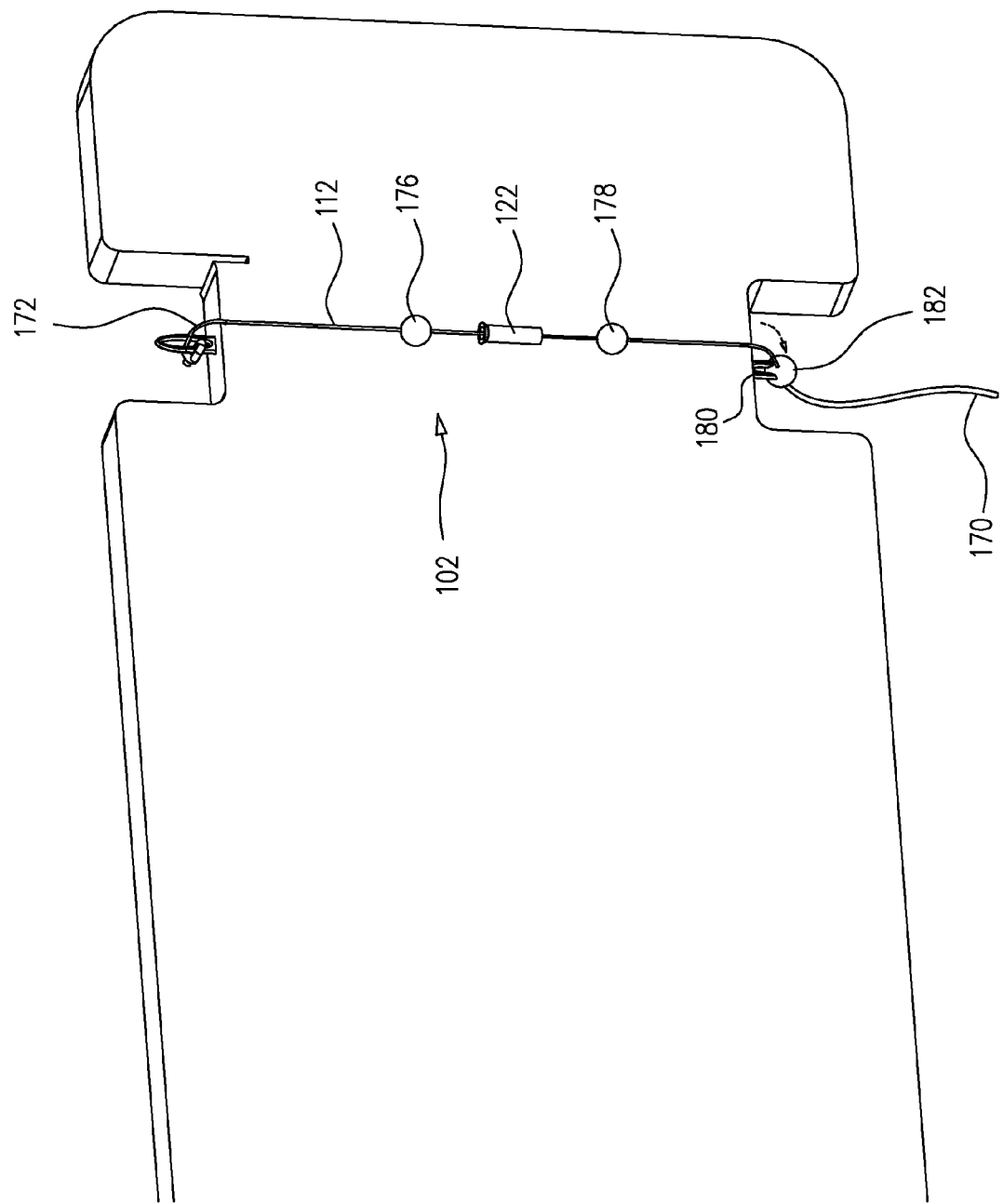

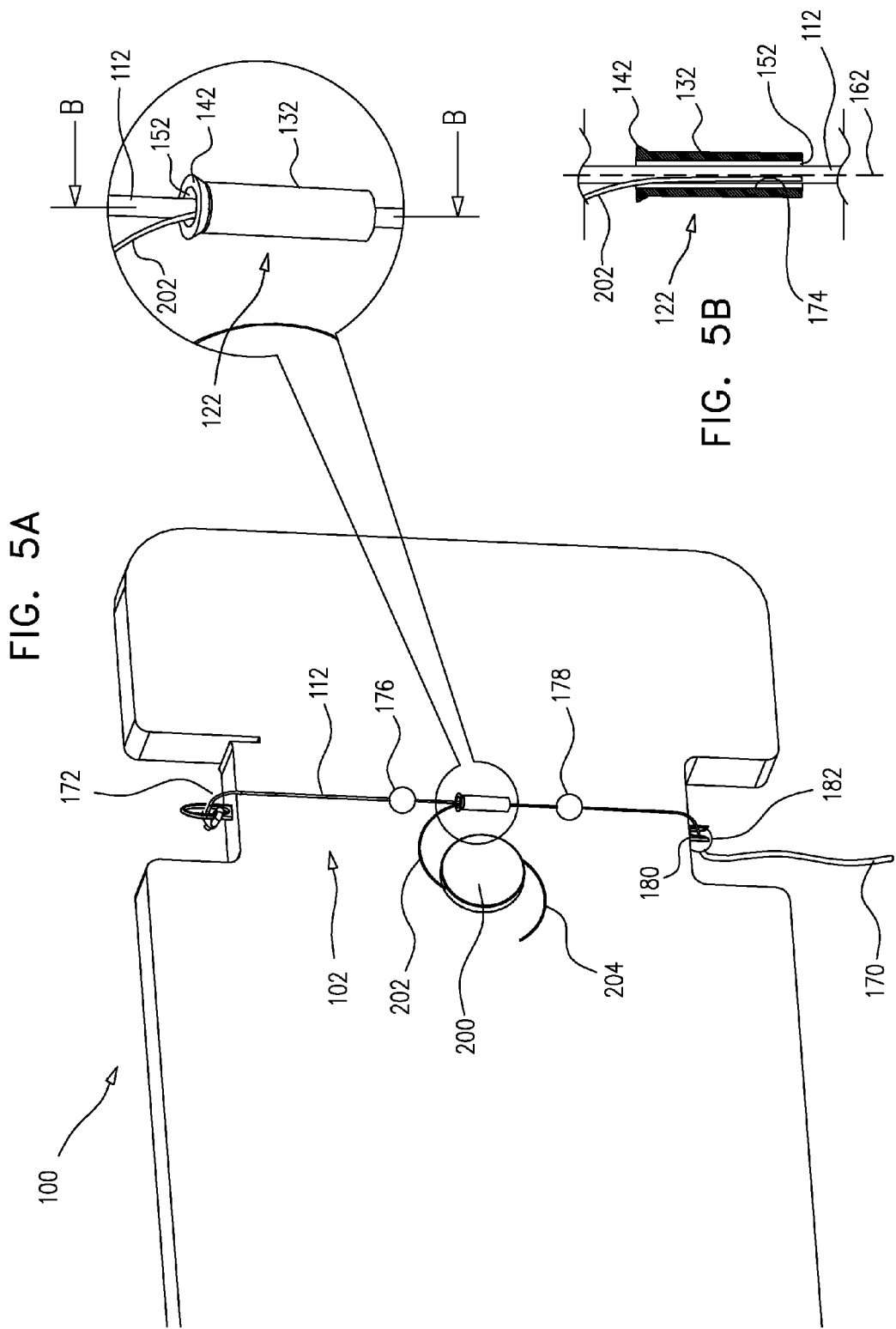

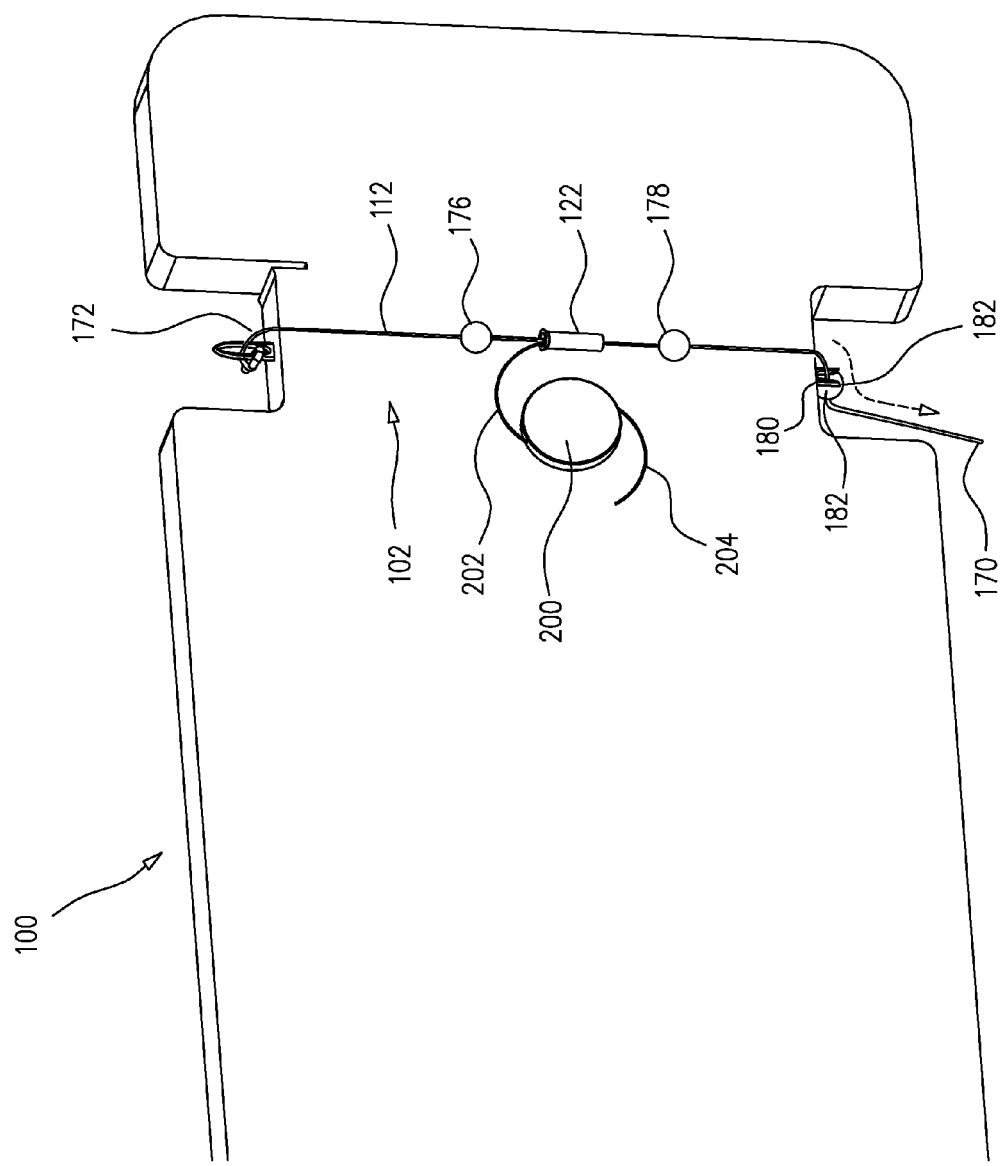

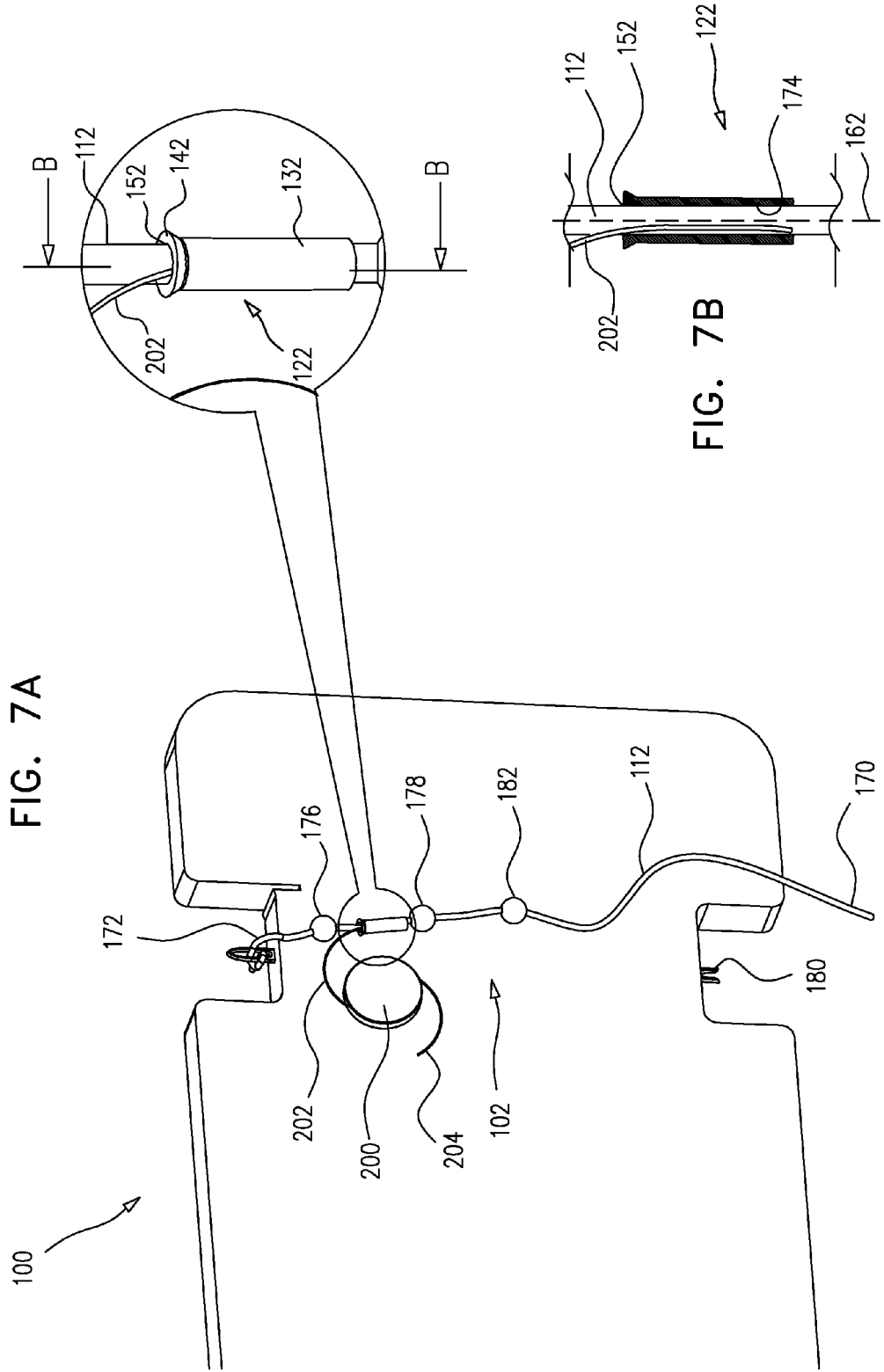

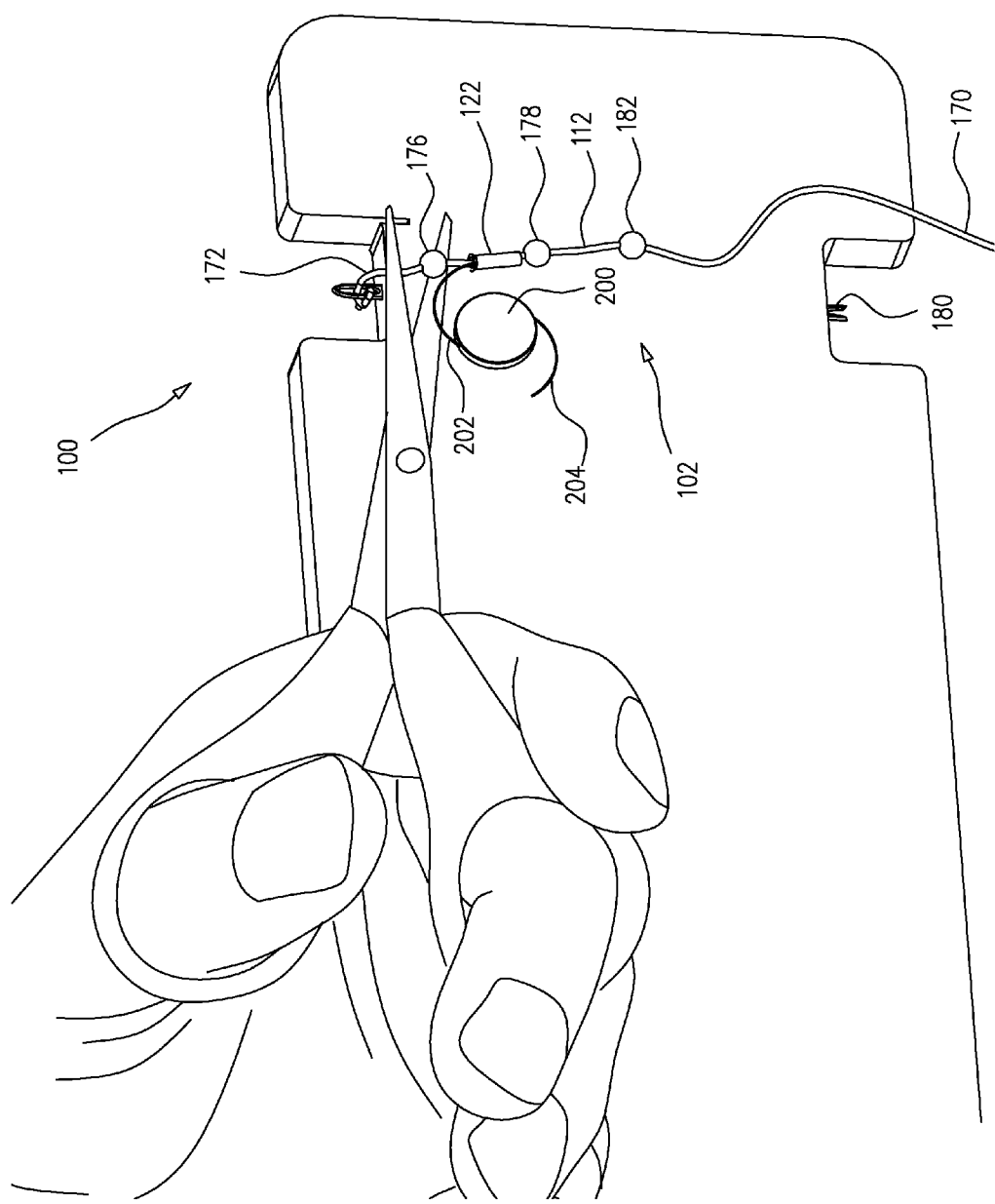

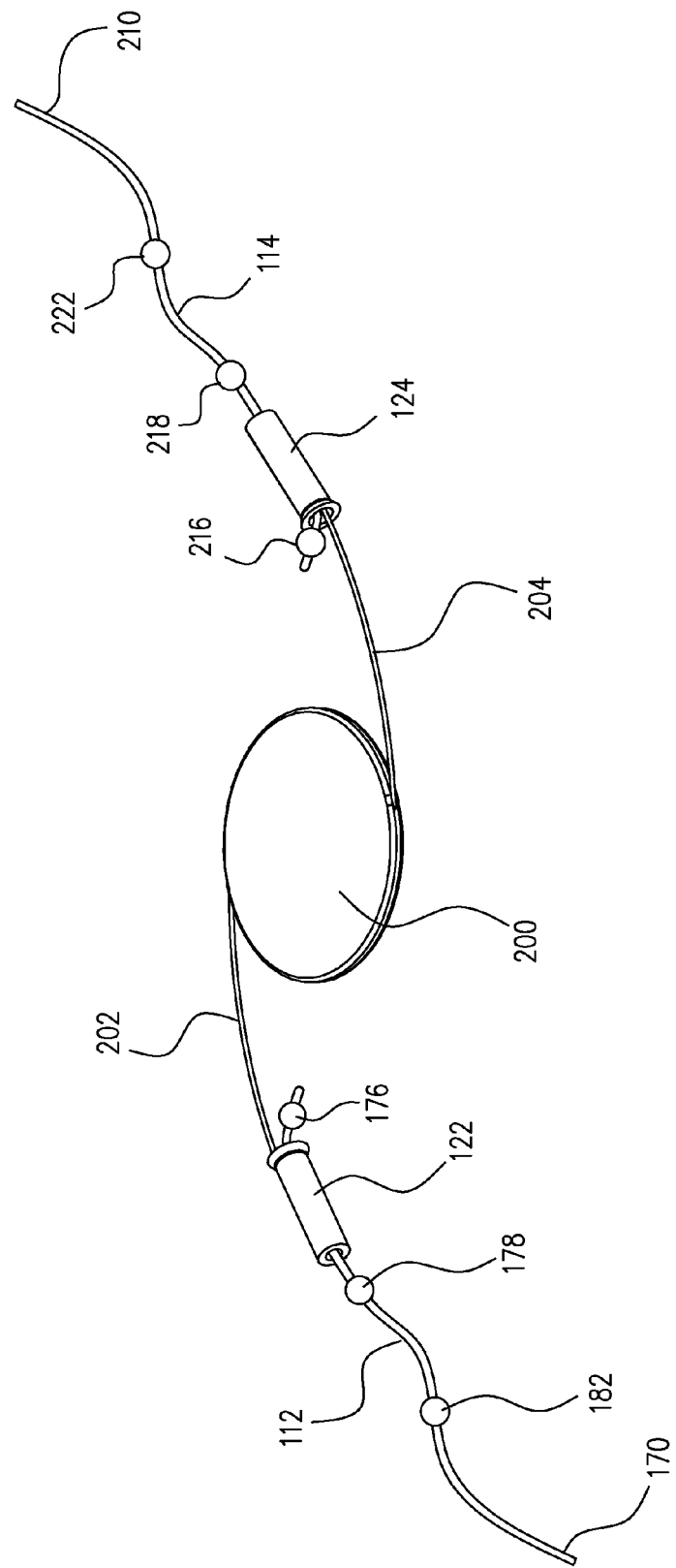

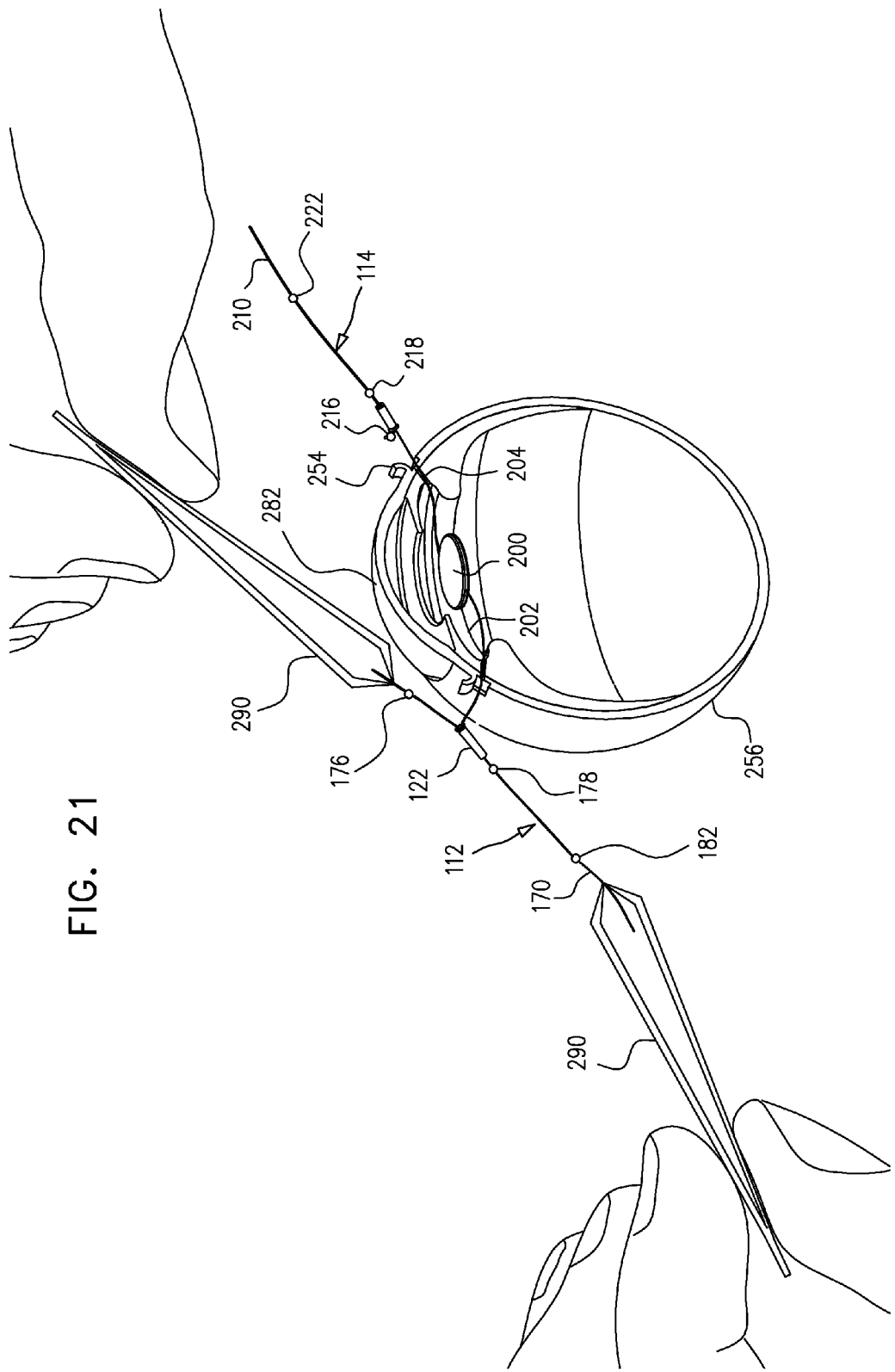

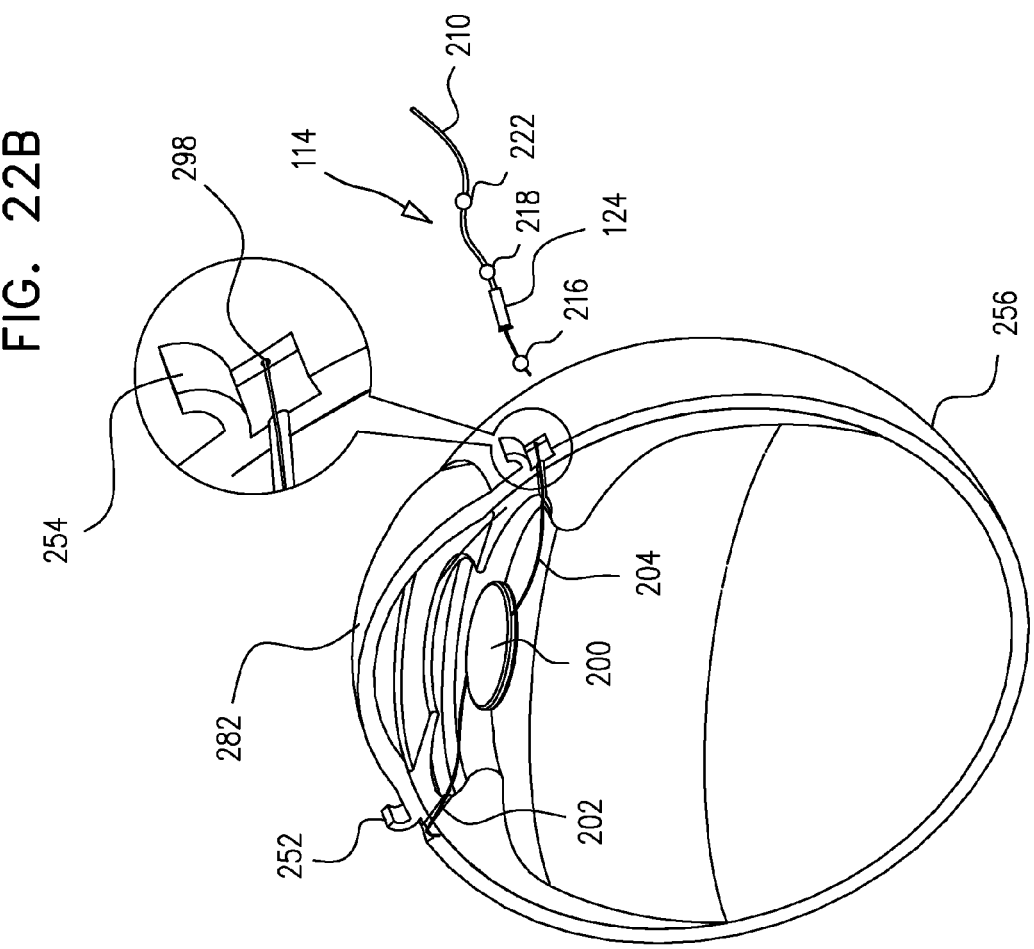

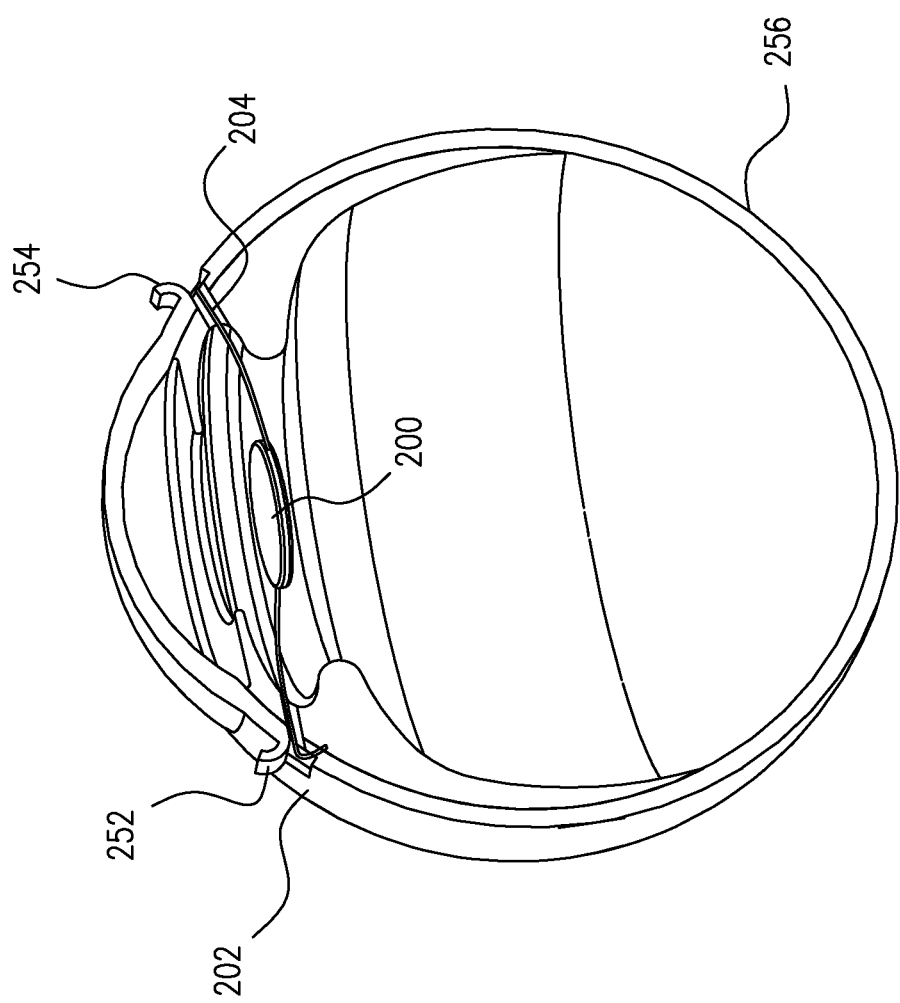

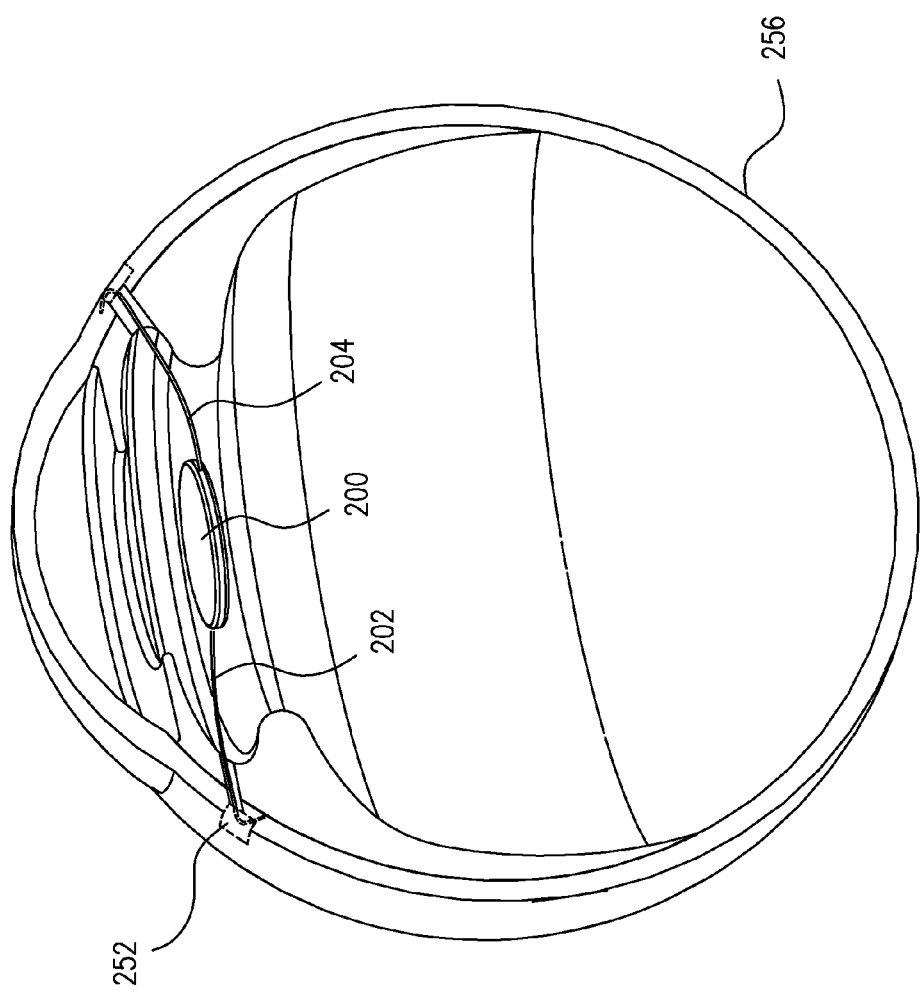

METHOD AND APPARATUS FOR PREPARATION AND INSERTION OF AN INTRAOCULAR LENS INTO THE EYE OF A PATIENT

FIELD OF THE INVENTION

The present invention relates generally to intraocular lenses and methods and apparatus for insertion thereof into the eye of a patient.

BACKGROUND OF THE INVENTION

Pseudophakic patients for whom the original ocular capsular bag is not intact, for example as a result of cataract surgery or lens exchange, require novel methods and apparatus for the implantation and fixation of an intraocular lens within the patient's eye.

SUMMARY OF THE INVENTION

The present invention seeks to provide methods and apparatus for the implantation and fixation of an intraocular lens within the patient's eye.

There is thus provided in accordance with a preferred embodiment of the present invention an apparatus for preparation of an intraocular lens assembly prior to insertion thereof into the eye of a patient, the apparatus including a pair of elongate stretchable loop extension assemblies each including an elongate stretchable loop extension element, whose thickness varies as a function of an extent to which it is stretched, and a connector through which the elongate stretchable loop extension element is threaded.

Preferably, the connector includes a longitudinal cylindrical bore formed therewithin, the elongate stretchable loop extension element being threaded through the longitudinal cylindrical bore. Preferably, the connector includes a cylindrical portion and a funnel shaped portion.

In accordance with an alternative embodiment of the present invention, the elongate stretchable loop extension element includes a pair of connector motion-limiting elements integrally formed thereon for retaining the connector therebetween in a partially pretensioned configuration, a section of the elongate stretchable loop extension element being stretchably threaded within the connector, thereby retaining the connector motion-limiting elements in tight engagement with the connector.

Preferably, when the elongate stretchable loop extension element is in an unstretched configuration, a diameter of the elongate stretchable loop extension element is generally equal to a diameter of the longitudinal cylindrical bore of the connector, thereby tightly engaging the elongate stretchable loop extension element with an inner surface of the longitudinal cylindrical bore of the connector, and thereby tightly retaining the connector in a fixed position on the elongate stretchable loop extension element.

Preferably, when the elongate stretchable loop extension element is in a stretched configuration, a diameter of the elongate stretchable loop extension element is narrower than a diameter of the longitudinal cylindrical bore, thereby releasing the elongate stretchable loop extension element from an inner surface of the longitudinal cylindrical bore of the connector, and allowing for insertion of at least one additional element into the longitudinal cylindrical bore of the connector.

Preferably, the elongate stretchable loop extension element includes a pair of connector motion-limiting elements integrally formed thereon for retaining the connector therebetween when the elongate stretchable loop extension element is in the stretched configuration.

Preferably, after inserting at least one additional element into the longitudinal cylindrical bore of the connector when the elongate stretchable loop extension element is in the stretched configuration and then allowing the elongate stretchable loop extension element to return to an unstretched fastened configuration, a diameter of the elongate stretchable loop extension element is generally equal to a diameter of the longitudinal cylindrical bore of the connector, thereby tightly engaging the elongate stretchable loop extension element and the at least one additional element with an inner surface of the cylindrical bore of the longitudinal cylindrical bore of the connector, and thereby fastening the at least one additional element to the elongate stretchable loop extension element.

There is also provided in accordance with another preferred embodiment of the present invention a method for insertion of an intraocular lens into the eye of a patient, the method including removably attaching loop extensions to loops of an intraocular lens prior to insertion of the intraocular lens into the eye of a patient, initially inserting into the eye of the patient the loop extensions, pulling on the loop extensions through sclerectomies formed in the sclera of the eye of the patient, inserting the intraocular lens into the eye of the patient, positioning the intraocular lens in a desired position in the eye of the patient by pulling on the loop extensions through the sclerectomies, and fixing the loops to the sclera of the eye of the patient at the sclerectomies and detaching the loop extensions from the loops.

Preferably, each loop extension of the loop extensions includes an elongate stretchable loop extension element formed of stretchable silicon, a thickness of the elongate stretchable loop extension element varying as a function of an extent to which the elongate stretchable loop extension element is stretched.

Preferably, each loop extension of the loop extensions also includes a corresponding connector having a longitudinal cylindrical bore formed therewithin, the elongate stretchable loop extension element of the loop extension being threaded through the longitudinal cylindrical bore. Preferably, each of the connectors includes a cylindrical portion and a funnel shaped portion.

In accordance with an alternative embodiment of the present invention, each of the elongate stretchable loop extension elements includes a pair of connector motion-limiting elements integrally formed thereon for retaining the corresponding connector therebetween in a partially pretensioned configuration, a section of the elongate stretchable loop extension element being stretchably threaded within the corresponding connector, thereby retaining the connector motion-limiting elements in tight engagement with the corresponding connector.

Preferably, removably attaching the loop extensions to the loops of the intraocular lens includes stretching and retaining the elongate stretchable loop extension element of each of the loop extensions from an unstretched unfastened configuration to a retained stretched configuration, while the elongate stretchable loop extension element is in the retained stretched configuration inserting an end of a corresponding one of the loops into the longitudinal cylindrical bore of the connector of the loop extension, and after inserting an end of a corresponding one of the loops into the longitudinal cylindrical bore of the connector of the loop extension, releasing the elongate stretchable loop extension element from the retained stretched configuration, thereby placing the elongate stretchable loop extension element in an unstretched fastened configuration.

Preferably, when the elongate stretchable loop extension element is in the unstretched unfastened configuration, a diameter of the elongate stretchable loop extension element is generally equal to a diameter of the longitudinal cylindrical bores of the corresponding connector, thereby tightly engaging the elongate stretchable loop extension element with an inner surface of the longitudinal cylindrical bore of the corresponding connector, and thereby tightly retaining the corresponding connector in a fixed position on the elongate stretchable loop extension element.

Preferably, when the elongate stretchable loop extension element is in the retained stretched configuration, a diameter of the elongate stretchable loop extension element is narrower than a diameter of the longitudinal cylindrical bore, thereby releasing the elongate stretchable loop extension element from an inner surface of the longitudinal cylindrical bore of the corresponding connector. Preferably, the elongate stretchable loop extension element includes a pair of connector motion-limiting elements integrally formed thereon for retaining the corresponding connector therebetween when the elongate stretchable loop extension element is in the retained stretched configuration.

Preferably, when the elongate stretchable loop extension element is in the unstretched fastened configuration, a diameter of the elongate stretchable loop extension element is generally equal to a diameter of the longitudinal cylindrical bore of the corresponding connector, thereby tightly engaging the elongate stretchable loop extension element and the loop with an inner surface of the cylindrical bore of the longitudinal cylindrical bore of the corresponding connector, and thereby fastening the loop to the elongate stretchable loop extension element.

Preferably, pulling on the loop extensions through the sclerectomies formed in the sclera of the eye of the patient includes pulling the elongate stretchable loop extension elements of the loop extensions, the corresponding connectors of the loop extensions and the corresponding loops of the intraocular lens from within the sclera through the sclerectomies. Preferably, once pulled through the sclerectomies, each connector of the connectors is operative to serve as a motion-limiting element which prevents a corresponding one of the loops, the connector and a corresponding one of the elongate stretchable loop extension elements from being retracted into the sclera.

Preferably, detaching the loop extension from the loop includes stretching the elongate stretchable loop extension element of the loop extension from the unstretched fastened configuration to a stretched unfastened configuration, and releasing the loop from the connector.

Preferably, when elongate stretchable loop extension element is in the stretched unfastened configuration, a diameter of the elongate stretchable loop extension element is narrower than a diameter of the longitudinal cylindrical bore of the corresponding connector, thereby releasing the elongate stretchable loop extension element and the loop from an inner surface of the longitudinal cylindrical bore of the corresponding connector.

There is further provided in accordance with yet another preferred embodiment of the present invention, a method of preparation of an intraocular lens assembly prior to insertion thereof into the eye of a patient, the method including removably attaching loop extensions to loops of an intraocular lens. Preferably, removably attaching loop extensions to loops of an intraocular lens includes providing a pair of elongate stretchable loop extension assemblies each including an elongate stretchable loop extension element, whose thickness varies as a function of an extent to which it is stretched and a connector through which the elongate stretchable loop extension element is threaded, and removably inserting an end of each loop of the intraocular lens into a corresponding connector of one of the pair of elongate stretchable loop extension assemblies.

Preferably, the connector includes a longitudinal cylindrical bore formed therewithin, the elongate stretchable loop extension element being threaded through the longitudinal cylindrical bore. Preferably, the connector includes a cylindrical portion and a funnel shaped portion.

In accordance with an alternative embodiment of the present invention, the elongate stretchable loop extension element includes a pair of connector motion-limiting elements integrally formed thereon for retaining the connector therebetween in a partially pretensioned configuration, a section of the elongate stretchable loop extension element being stretchably threaded within the connector, thereby retaining the connector motion-limiting elements in tight engagement with the connector.

Preferably, removably inserting an end of each loop of the intraocular lens into a corresponding connector of one of the pair of elongate stretchable loop extension assemblies includes stretching and retaining the elongate stretchable loop extension element of each of the elongate stretchable loop extension assemblies from an unstretched unfastened configuration to a retained stretched configuration, while the elongate stretchable loop extension element is in the retained stretched configuration inserting an end of the loop into the longitudinal cylindrical bore of the corresponding connector of one of the pair of elongate stretchable loop extension assemblies, and after inserting an end of the loop into the longitudinal cylindrical bore of the corresponding connector of one of the pair of elongate stretchable loop extension assemblies, releasing the elongate stretchable loop extension element from the retained stretched configuration, thereby placing the elongate stretchable loop extension element in an unstretched fastened configuration.

Preferably, when the elongate stretchable loop extension element is in the unstretched unfastened configuration, a diameter of the elongate stretchable loop extension element is generally equal to a diameter of the longitudinal cylindrical bore of the connector, thereby tightly engaging the elongate stretchable loop extension element with an inner surface of the longitudinal cylindrical bore of the connector, and thereby tightly retaining the connector in a fixed position on the elongate stretchable loop extension element.

Preferably, when the elongate stretchable loop extension element is in the retained stretched configuration, a diameter of the elongate stretchable loop extension element is narrower than a diameter of the longitudinal cylindrical bore, thereby releasing the elongate stretchable loop extension element from an inner surface of the longitudinal cylindrical bore of the connector. Preferably, the elongate stretchable loop extension element includes a pair of connector motion-limiting elements integrally formed thereon for retaining the connector therebetween when the elongate stretchable loop extension element is in the retained stretched configuration.

Preferably, when the elongate stretchable loop extension element is in the unstretched fastened configuration, a diameter of the elongate stretchable loop extension element is generally equal to a diameter of the longitudinal cylindrical bore of the connector, thereby tightly engaging the elongate stretchable loop extension element and the loop with an inner surface of the cylindrical bore of the longitudinal cylindrical bore of the connector, and thereby fastening the loop to the elongate stretchable loop extension element.

BRIEF DESCRIPTION OF THE DRAWINGS

The present invention will be understood and appreciated more fully from the following detailed description taken in conjunction with the drawings in which:

FIG. 1A is a simplified pictorial illustration of an apparatus for preparation of an intraocular lens assembly, constructed in accordance with a preferred embodiment of the present invention;

FIG. 1B is a simplified sectional view of a connector which is part of the apparatus of FIG. 1A, the sectional view being taken along lines B-B of FIG. 1A;

FIG. 1C is a simplified pictorial illustration of an apparatus for preparation of an intraocular lens assembly, constructed in accordance with an alternative embodiment of the present invention;

FIG. 1D is a simplified sectional view of a connector which is part of the apparatus of FIG. 1C, the sectional view being taken along lines D-D of FIG. 1C;

FIG. 2A is a simplified pictorial illustration of a first step in the operation of the apparatus of FIGS. 1A & 1B;

FIG. 2B is a simplified sectional view of a connector which is part of the apparatus of FIGS. 1A & 1B, the sectional view being taken along lines B-B of FIG. 2A;

FIG. 3A is a simplified pictorial illustration of a second step in the operation of the apparatus of FIGS. 1A & 1B;

FIG. 3B is a simplified sectional view of a connector which is part of the apparatus of FIG. 1, the sectional view being taken along lines B-B of FIG. 3A;

FIG. 4 is a simplified pictorial illustration of a third step in the operation of the apparatus of FIGS. 1A & 1B;

FIG. 5A is a simplified pictorial illustration of a fourth step in the operation of the apparatus of FIGS. 1A & 1B;

FIG. 5B is a simplified sectional view of a connector which is part of the apparatus of FIG. 1, the sectional view being taken along lines B-B of FIG. 5A;

FIG. 6 is a simplified pictorial illustration of a fifth step in the operation of the apparatus of FIGS. 1A & 1B;

FIG. 7A is a simplified pictorial illustration of a sixth step in the operation of the apparatus of FIGS. 1A & 1B;

FIG. 7B is a simplified sectional view of a connector which is part of the apparatus of FIG. 1, the sectional view being taken along lines B-B of FIG. 7A;

FIG. 8 is a simplified pictorial illustration of a seventh step in the operation of the apparatus of FIGS. 1A & 1B;

FIG. 16 is a simplified pictorial illustration of an example of an intraocular lens assembly prepared by employing the apparatus of FIG. 1;

FIG. 21 is a simplified pictorial illustration of a fourth step in the implanting of an intraocular lens which is part of the intraocular lens assembly of FIG. 16 into an eye of a patient;

FIGS. 22A and 22B are simplified pictorial illustrations of a fifth step in the implanting of an intraocular lens which is part of the intraocular lens assembly of FIG. 16 into an eye of a patient;

FIG. 23 is a simplified pictorial illustration of a sixth step in the implanting of an intraocular lens which is part of the intraocular lens assembly of FIG. 16 into an eye of a patient;

FIG. 25 is a simplified pictorial illustration of an eighth step in the implanting of an intraocular lens which is part of the intraocular lens assembly of FIG. 16 into an eye of a patient.

DETAILED DESCRIPTION OF PREFERRED EMBODIMENTS

Figure 9:
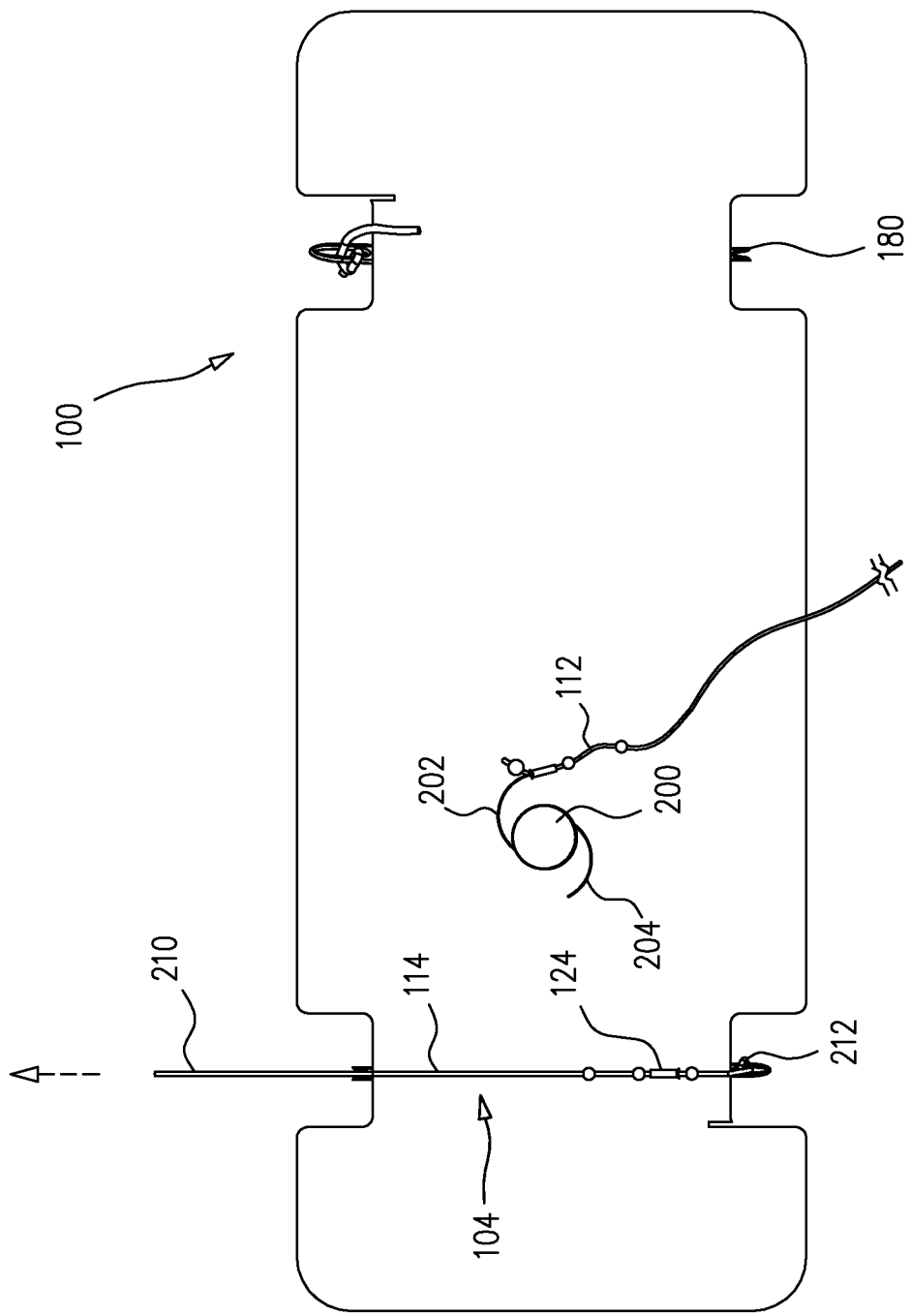
FIG. 9 is a simplified pictorial illustration of an eighth step in the operation of the apparatus of FIGS. 1A & 1B.

Reference is now made to FIG. 1A, which is a simplified pictorial illustration of an apparatus for preparation of an intraocular lens assembly, constructed in accordance with a preferred embodiment of the present invention, and to FIG. 1B, which is a simplified sectional view of a connector which is part of the apparatus of FIG. 1A, the sectional view being taken along lines B-B of FIG. 1A. The novel apparatus and surgical procedure associated therewith and described hereinbelow, in which an intraocular lens is placed within the sulcus of a patient's eye and thereafter fixed to the sclera of the eye, is particularly suitable for pseudophakic patients for whom the capsular bag is not intact, for example as a result of cataract surgery or lens exchange. It is appreciated that this novel apparatus and surgical procedure is also suitable for any surgical procedure which involves implantation of intraocular devices such as, for example, an artificial iris or an intraocular telescopic lens.

As shown in FIGS. 1A & 1B, the apparatus 100 includes a pair of elongate stretchable loop extension assemblies 102 and 104, which include corresponding elongate stretchable loop extension elements 112 and 114, preferably formed of silicon, and whose thickness varies as a function of an extent to which it is stretched. Elongate stretchable loop extension assemblies 102 and 104 also include corresponding connectors 122 and 124 through which corresponding elongate stretchable loop extension elements 112 and 114 are threaded. Connectors 122 and 124 preferably include corresponding cylindrical portions 132 and 134 and corresponding funnel shaped portions 142 and 144. Cylindrical bores 152 and 154 are preferably formed within respective connectors 122 and 124 along corresponding axes 162 and 164.

Reference is now made to FIG. 1C, which is a simplified pictorial illustration of apparatus 100 constructed in accordance with an alternative embodiment of the present invention, and to FIG. 1D, which is a simplified sectional view of connector 122 of apparatus 100 of FIG. 1C, the sectional view being taken along lines D-D of FIG. 1C.

As shown in the alternative embodiment of FIGS. 1C & 1D, connector motion-limiting elements 166 and 168 are formed on elongate stretchable loop extension element 112 for retaining connector 122 therebetween in a partially pre-tensioned configuration, wherein a section of elongate stretchable loop extension element 112 disposed within connector 122 is stretched, thereby retaining elements 166 and 168 in tight engagement with connector 122.

Reference is now made to FIGS. 2A, 3A, 4, 5A, 6, 7A, 8, 9, 10, 11, 12, 13, 14 and 15, which are simplified pictorial illustrations of steps in the operation of apparatus 100, and to FIGS. 2B, 3B, 5B and 7B which are simplified sectional views of connector 122, the sectional view being taken along lines B-B of respective FIGS. 2A, 3A, 5A and 7A. It is appreciated that although FIGS. 2A-15 illustrate steps in the operation of apparatus 100 as illustrated in the embodiment of FIGS. 1A & 1B, the same steps may be executed in the operation of apparatus 100 as illustrated in the alternative embodiment of FIGS. 1C & 1D.

As shown in FIG. 2A, in the first step in the operation of apparatus 100, elongate stretchable loop extension element 112 of elongate stretchable loop extension assembly 102 is unwound from the apparatus 100 to an unstretched configuration. As clearly seen in the unwound configuration of FIG. 2A, elongate stretchable loop extension element 112 has a loose end 170 and a retained end 172 retained on apparatus 100.

It is a particular feature of this preferred embodiment of the present invention that in the unstretched configuration of FIGS. 2A & 2B, the diameter of elongate stretchable loop extension element 112 is generally equal to the diameter of cylindrical bore 152, thereby tightly engaging elongate stretchable loop extension element 112 with an inner surface 174 of cylindrical bore 152, and thereby tightly retaining connector 122 in a fixed position on elongate stretchable loop extension element 112.

As further shown in FIG. 3A, in the second step in the operation of apparatus 100, elongate stretchable loop extension element 112 of elongate stretchable loop extension assembly 102 is stretched from the apparatus 100 to a stretched configuration by a user pulling on loose end 170.

It is a another particular feature of this preferred embodiment of the present invention that in the stretched configuration of FIGS. 3A & 3B, the diameter of elongate stretchable loop extension element 112 is narrower than the diameter of cylindrical bore 152, thereby releasing elongate stretchable loop extension element 112 from inner surface 174 of cylindrical bore 152, and thereby allowing insertion of additional elements into connector 122. A pair of connector motion-limiting elements 176 and 178 are formed on elongate stretchable loop extension element 112 for retaining connector 122 therebetween on elongate stretchable loop extension element 112.

Turning now to FIG. 4, it is shown that in the third step in the operation of apparatus 100, loose end 170 of elongate stretchable loop extension element 112 is further stretched through a fork-shaped retaining element 180 formed on apparatus 100 and is retained therein by an extension element retaining element 182 formed on elongate stretchable loop extension element 112.

As further shown in FIGS. 5A & 5B, in a fourth step of the operation of apparatus 100, an intraocular lens 200 having loops 202 and 204 is brought into close proximity to elongate stretchable loop extension element 112, and loop 202 is inserted into bore 152 of connector 122 via funnel shaped portion 142. It is appreciated that loops 202 and 204 may be oriented either clockwise or counterclockwise with respect to intraocular lens 200. As described hereinabove, in the stretched configuration, the diameter of elongate stretchable loop extension element 112 is narrower than the diameter of cylindrical bore 152, thereby allowing insertion of elements other than elongate stretchable loop extension element 112 into connector 122.

Thereafter, in a fifth step of the operation of apparatus 100 shown in FIG. 6, extension element retaining element 182 is released from fork-shaped retaining element 180 of apparatus 100, thereby releasing elongate stretchable loop extension element 112. As further shown in FIGS. 7A & 7B, in a sixth step of the operation of apparatus 100, release of elongate stretchable loop extension element 112 from fork-shaped retaining element 180 allows elongate stretchable loop extension element 112 to return to the unstretched configuration wherein the diameter of elongate stretchable loop extension element 112 is generally equal to the diameter of cylindrical bore 152, thereby tightly engaging elongate stretchable loop extension element 112 and loop 202 with inner surface 174 of cylindrical bore 152, and thereby fastening loop 202 to elongate stretchable loop extension element 112.

Thereafter, as shown in FIG. 8, in a seventh step of the operation of apparatus 100, the user of apparatus 100 preferably employs a pair of surgical scissors to sever elongate stretchable loop extension element 112 between retained end 172 and connector motion-limiting element 176, thereby disconnecting elongate stretchable loop extension element 112 along with loop 202 connected thereto, from apparatus 100.

Turning now to FIG. 9, it is shown that in an eighth step of the operation of apparatus 100, elongate stretchable loop extension element 114 of elongate stretchable loop extension assembly 104 is unwound from the apparatus 100 to an unstretched configuration. As clearly seen in FIG. 9, in the unwound configuration, elongate stretchable loop extension element 114 has a loose end 210 and a retained end 212 retained on apparatus 100.

As described hereinabove with reference to FIGS. 2A and 2B, it is a particular feature of this preferred embodiment of the present invention that in the unstretched configuration of FIG. 9, the diameter of elongate stretchable loop extension element 114 is generally equal to the diameter of cylindrical bore 154 of connector 124, thereby tightly engaging elongate stretchable loop extension element 114 with an inner surface 214 of cylindrical bore 154, and thereby tightly retaining connector 124 in a fixed position on elongate stretchable loop extension element 114.

Figure 10:
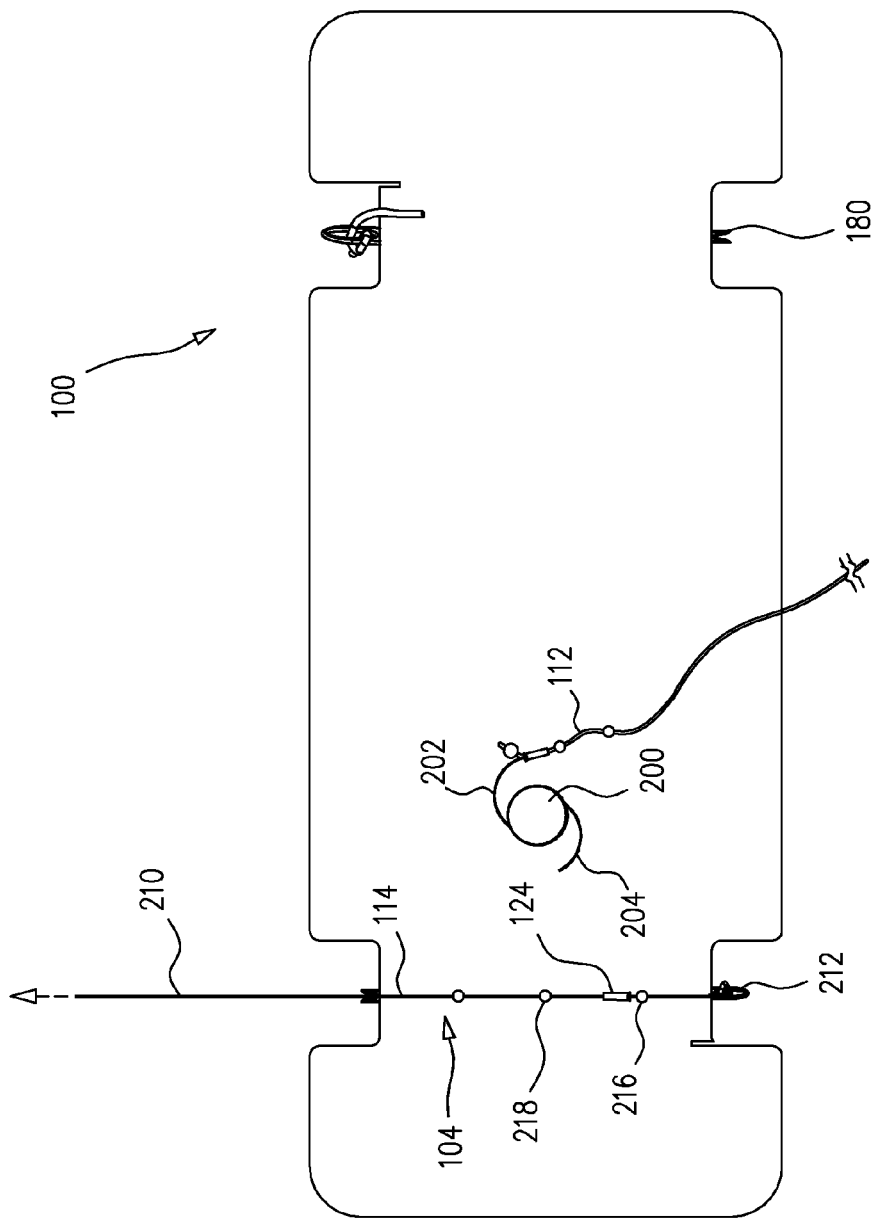
FIG. 10 is a simplified pictorial illustration of a ninth step in the operation of the apparatus of FIGS. 1A & 1B.

Thereafter, in a ninth step of the operation of apparatus 100 shown in FIG. 10, elongate stretchable loop extension element 114 of elongate stretchable loop extension assembly 104 is stretched from the apparatus 100 to a stretched configuration by a user pulling on loose end 210.

As described hereinabove with reference to FIGS. 3A and 3B, it is a particular feature of this preferred embodiment of the present invention that in the stretched configuration of FIG. 10, the diameter of elongate stretchable loop extension element 114 is narrower than the diameter of cylindrical bore 154, thereby releasing elongate stretchable loop extension element 114 from inner surface 214 of cylindrical bore 154, and thereby allowing insertion of additional elements into connector 124. A pair of connector motion-limiting elements 216 and 218 are formed on elongate stretchable loop extension element 114 for retaining connector 124 therebetween on elongate stretchable loop extension element 114.

Figure 11:
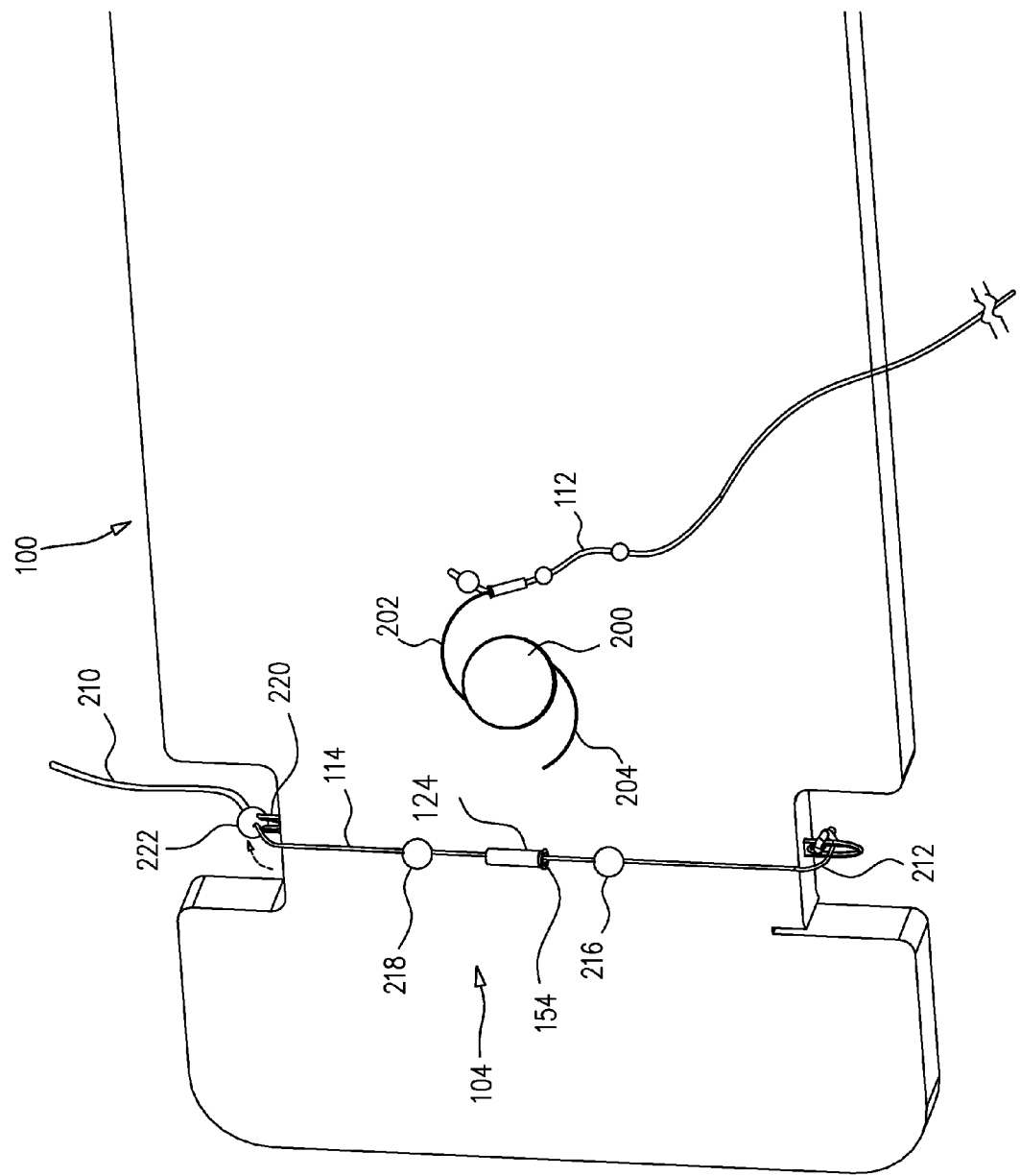
FIG. 11 is a simplified pictorial illustration of a tenth step in the operation of the apparatus of FIGS. 1A & 1B.

Turning now to FIG. 11, it is shown that in the tenth step in the operation of apparatus 100, loose end 210 of elongate stretchable loop extension element 114 is further stretched through a fork-shaped retaining element 220 formed on apparatus 100 and is retained therein by an extension element retaining element 222 formed on elongate stretchable loop extension element 114.

Figure 12:
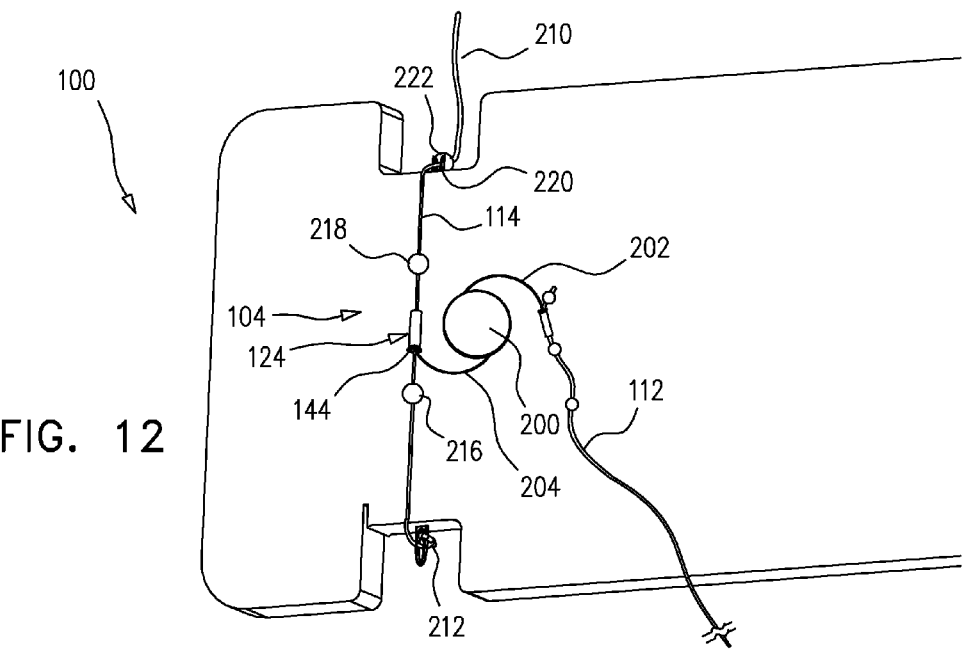
FIG. 12 is a simplified pictorial illustration of an eleventh step in the operation of the apparatus of FIGS. 1A & 1B.

Thereafter, in an eleventh step of the operation of apparatus 100 shown in FIG. 12, intraocular lens 200 is brought into close proximity to elongate stretchable loop extension element 114, and loop 204 is inserted into bore 154 of connector 124 via funnel shaped portion 144. As described hereinabove, in the stretched configuration, the diameter of elongate stretchable loop extension element 114 is narrower than the diameter of cylindrical bore 154, thereby allowing insertion of elements other than elongate stretchable loop extension element 114 into connector 124.

Figure 13:
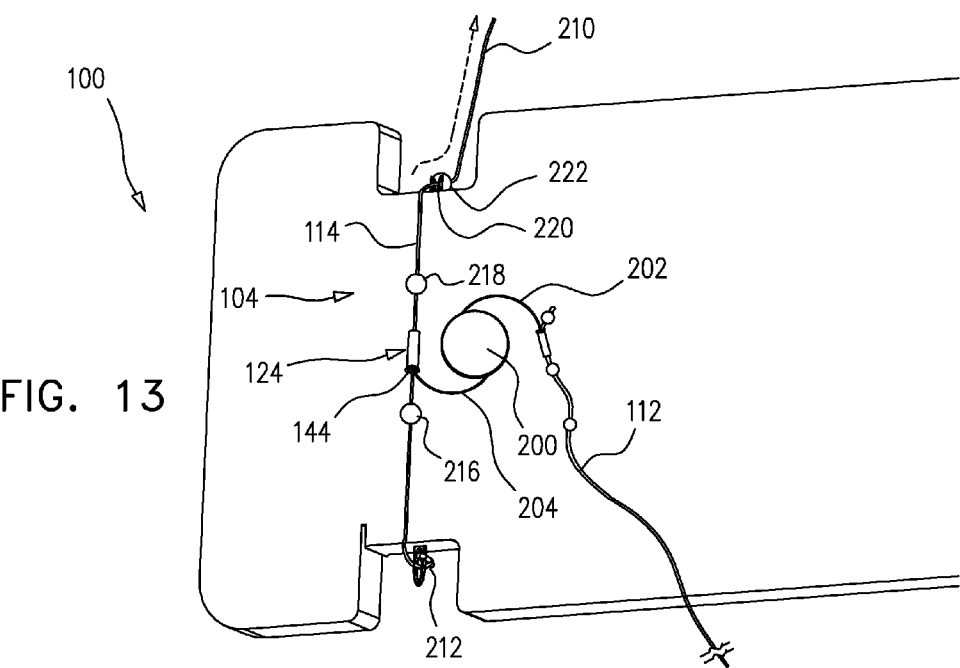
FIG. 13 is a simplified pictorial illustration of a twelfth step in the operation of the apparatus of FIGS. 1A & 1B.
Figure 14:
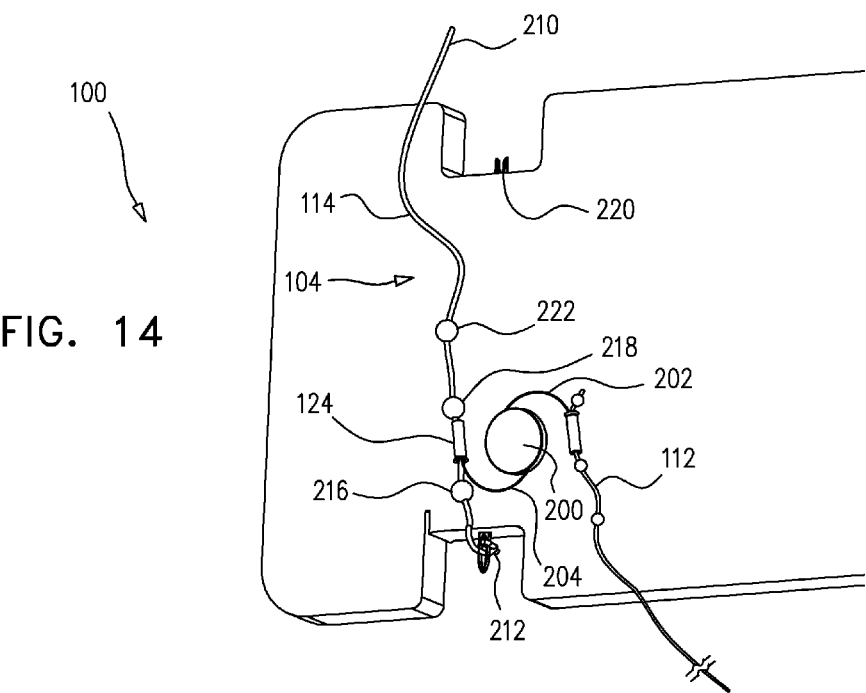
FIG. 14 is a simplified pictorial illustration of a thirteenth step in the operation of the apparatus of FIGS. 1A & 1B.

Turning now to FIG. 13, it is shown that in a twelfth step of the operation of apparatus 100, extension element retaining element 222 is released from fork-shaped retaining element 220 of apparatus 100, thereby releasing elongate stretchable loop extension element 114. As further shown in FIG. 14, in a thirteenth step of the operation of apparatus 100, release of elongate stretchable loop extension element 114 from fork-shaped retaining element 220 allows elongate stretchable loop extension element 114 to return to the unstretched configuration wherein the diameter of elongate stretchable loop extension element 114 is generally equal to the diameter of cylindrical bore 154, thereby tightly engaging elongate stretchable loop extension element 114 and loop 204 with inner surface 214 of cylindrical bore 154, and thereby fastening loop 204 to elongate stretchable loop extension element 114.

Figure 15:
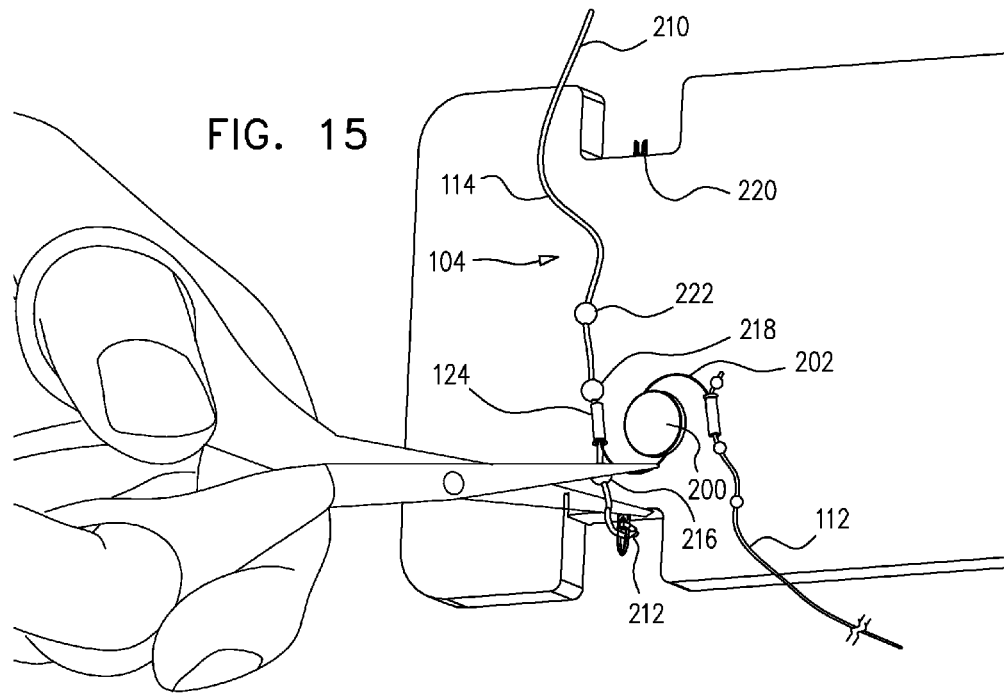
FIG. 15 is a simplified pictorial illustration of a fourteenth step in the operation of the apparatus of FIGS. 1A & 1B.

Thereafter, in a fourteenth step of the operation of apparatus 100 shown in FIG. 15, the user of apparatus 100 preferably employs a pair of surgical scissors to sever elongate stretchable loop extension element 114 between retained end 212 and connector motion-limiting element 216, thereby disconnecting elongate stretchable loop extension element 114 along with loop 204 connected thereto, from apparatus 100.

Reference is now made to FIG. 16, which is a simplified pictorial illustration of an example of an intraocular lens assembly prepared by employing the apparatus of FIG. 1. As shown in FIG. 16, loop 202 of intraocular lens 200 is fastened to unstretched elongate stretchable loop extension element 112 within connector 122 and loop 204 of intraocular lens 200 is fastened to unstretched elongate stretchable loop extension element 114 within connector 124.

It is appreciated that in the orientation of FIG. 16, intraocular lens 200 along with loops 202 and 204 is in an inverted configuration relative to the configuration of FIGS. 1A-15. In the configuration of FIG. 16, loop 202 serves as a leading left-hand loop when implanting intraocular lens 200 into an eye of a patient, as will be described hereinbelow with reference to FIGS. 18-25.

Figure 17A:
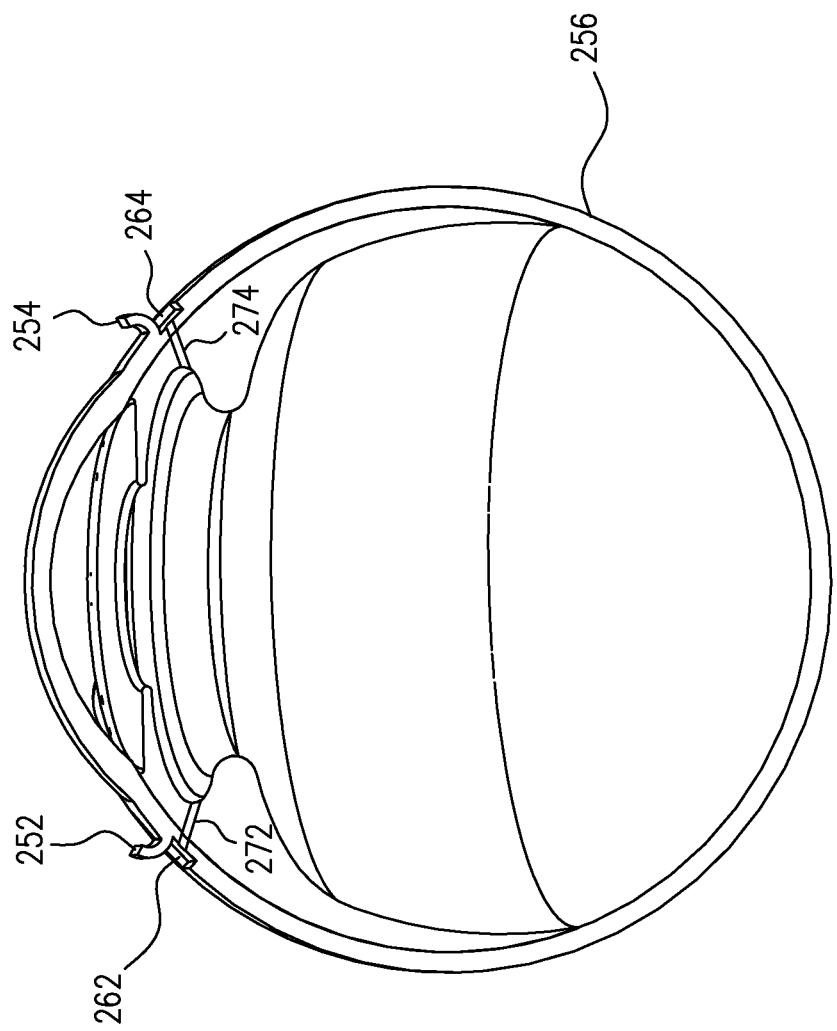
FIGS. 17A and 17B are simplified pictorial illustrations of an eye of a patient prepared for insertion of an intraocular lens which is part of the intraocular lens assembly of FIG. 16.
Figure 17B:
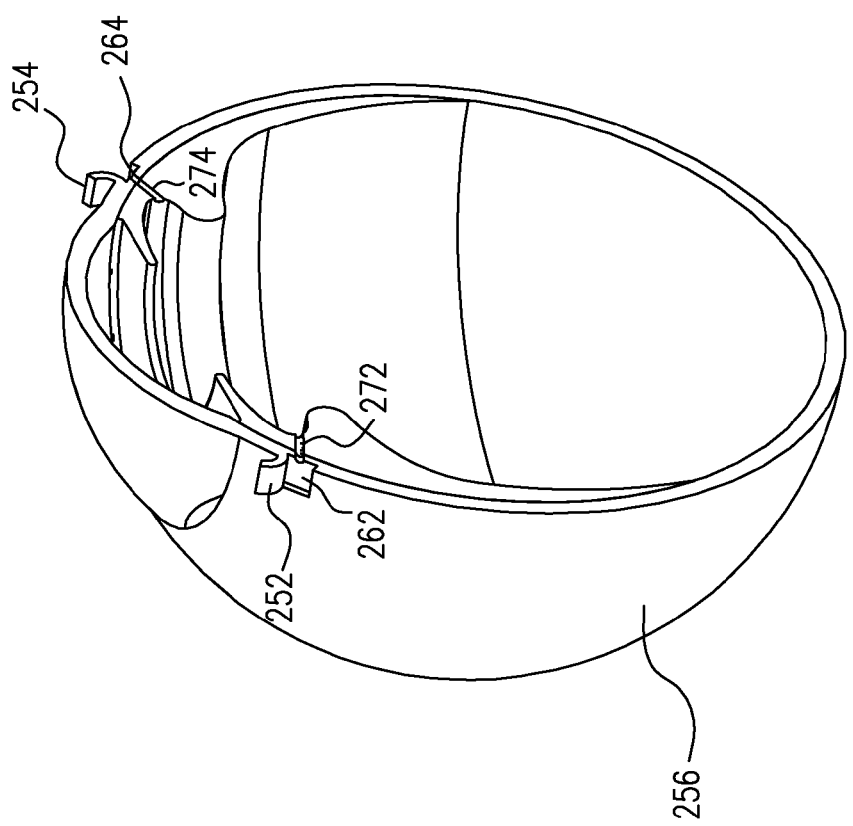

Reference is now made to FIGS. 17A and 17B, which are simplified pictorial illustrations of a human eye prepared for insertion of an intraocular lens by sclerectomy. As shown in FIGS. 17A and 17B, in preparation for insertion of intraocular lens 200, a pair of scleral flaps 252 and 254 are surgically formed on both sides of the sclera 256 of the eye, thereby forming corresponding recesses 262 and 264. Sclerectomies 272 and 274 which communicate between corresponding recesses 262 and 264 and the interior of sclera 256 are also surgically formed.

As described hereinabove, the novel procedure described hereinbelow in which intraocular lens 200 will be placed within the sulcus and fixed to the sclera is particularly suitable for pseudophakic patients for whom the capsular bag is not intact, for example as a result of cataract surgery or lens exchange.

Reference is now made to FIGS. 18, 19, 20, 21, 22A, 22B, 23, 24 and 25, which are simplified pictorial illustrations of steps in the implantation of an intraocular lens which is part of the intraocular lens assembly of FIG. 16 into an eye of a patient.

Figure 18:
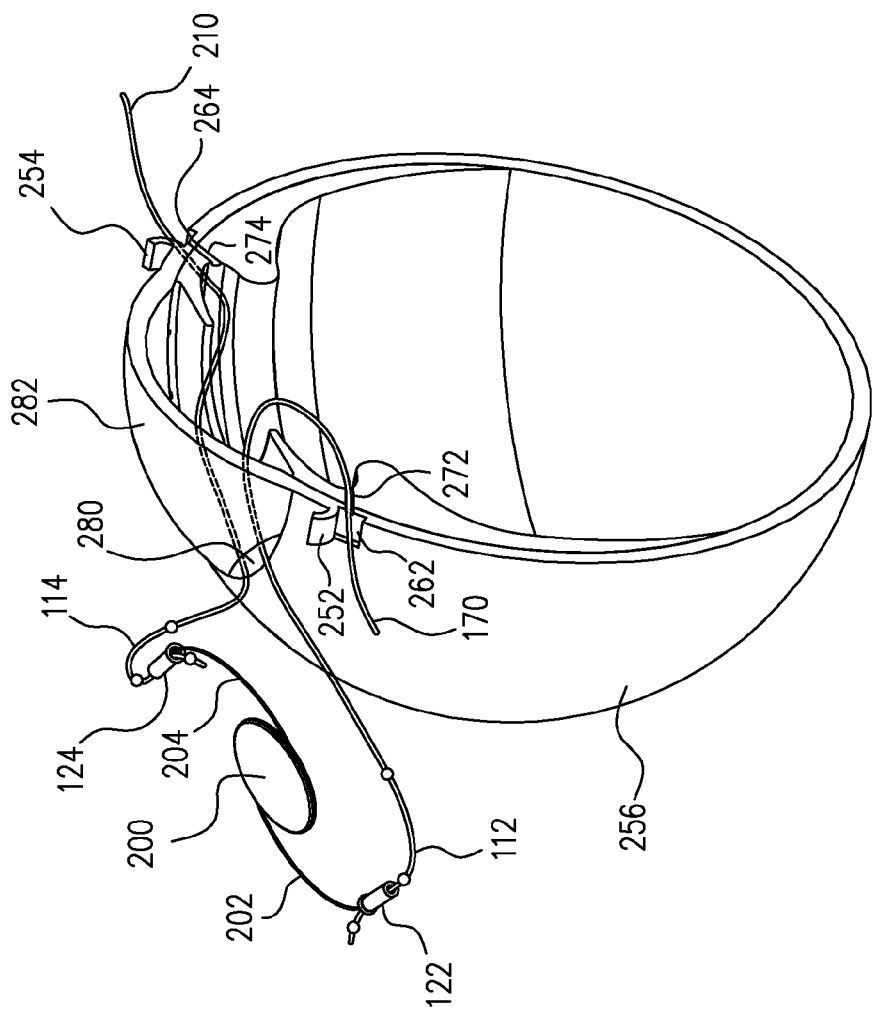
FIG. 18 is a simplified pictorial illustration of a first step in the implanting of an intraocular lens which is part of the intraocular lens assembly of FIG. 16 into an eye of a patient.
Figure 19:
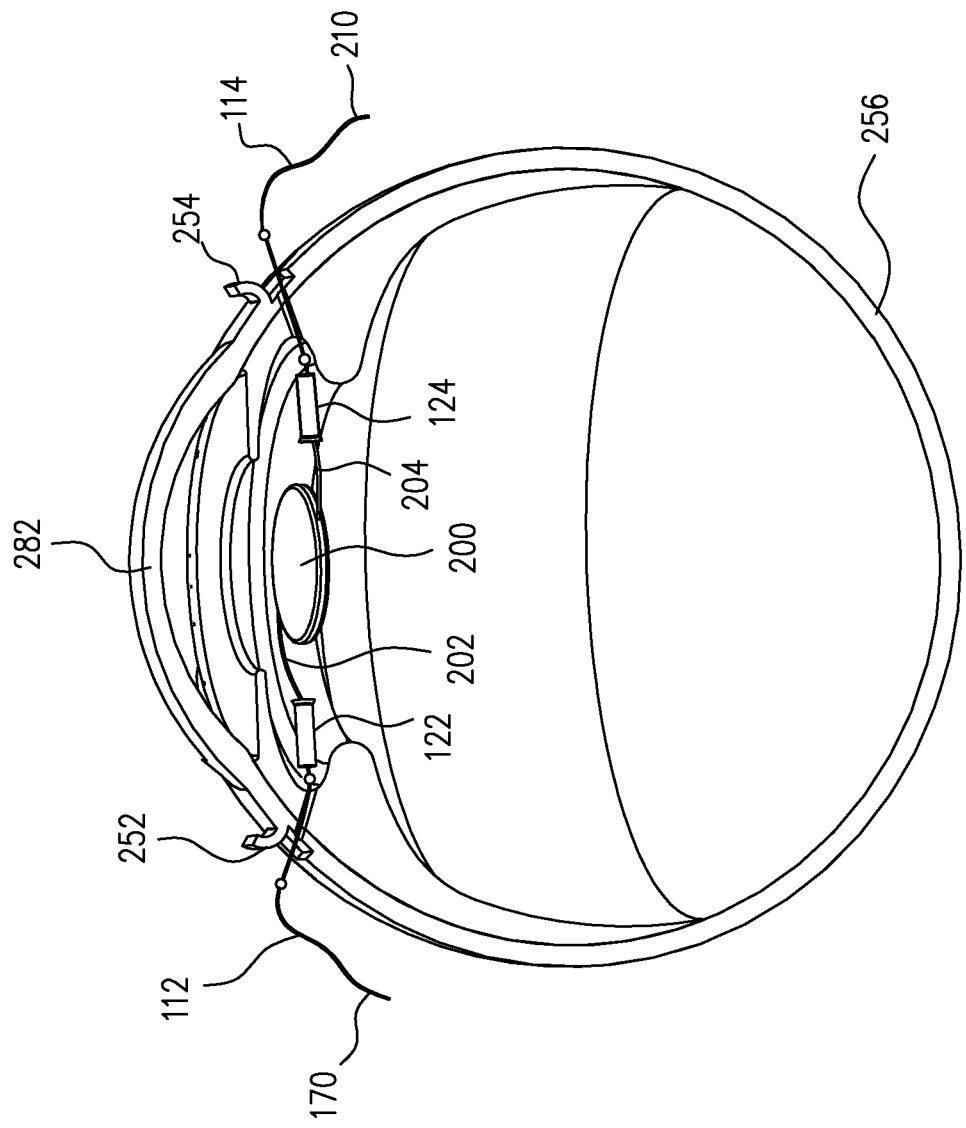
FIG. 19 is a simplified pictorial illustration of a second step in the implanting of an intraocular lens which is part of the intraocular lens assembly of FIG. 16 into an eye of a patient.

As shown in the first step of FIG. 18, loose ends 170 and 210 of corresponding stretchable loop extension elements 112 and 114 are inserted into the eye via a limbal cut 280 surgically formed between the cornea 282 and the sclera 256, and are pulled through sclerectomies 272 and 274, respectively, by intraocular forceps. Intraocular lens 200 is then inserted through limbal cut 280 to the position shown in FIG. 19.

Figure 20:
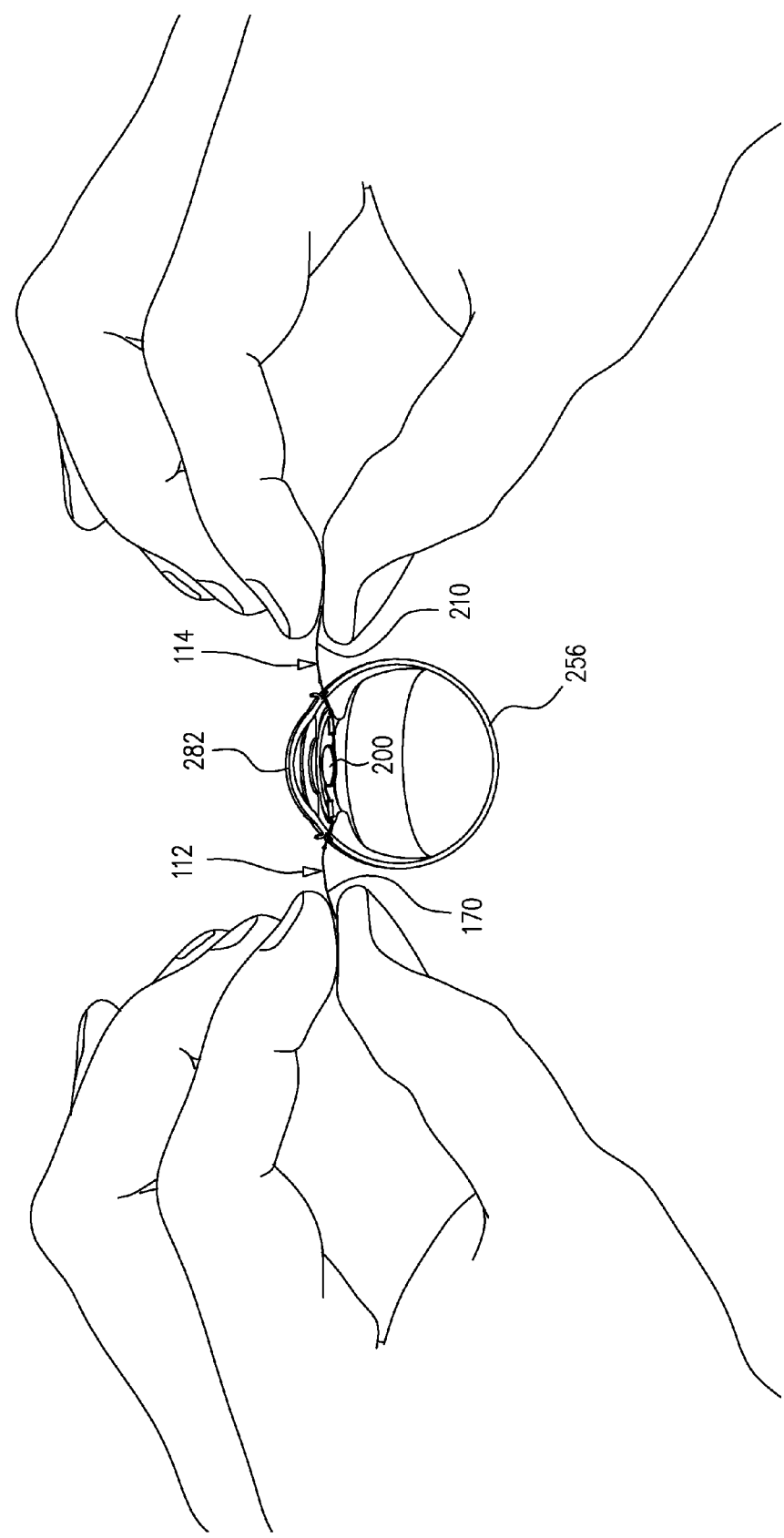
FIG. 20 is a simplified pictorial illustration of a third step in the implanting of an intraocular lens which is part of the intraocular lens assembly of FIG. 16 into an eye of a patient.

Thereafter, as shown in FIG. 20, loose ends 170 and 210 of corresponding stretchable loop extension elements 112 and 114 are further completely pulled through sclerectomies 272 and 274, respectively, thereby pulling respective connectors 122 and 124 along with loops 202 and 204 from within sclera 256 through sclerectomies 272 and 274, respectively.

It is a particular feature of the present invention that once pulled through sclerectomies 272 and 274, connectors 122 and 124 are operative to serve as motion-limiting elements which prevent loops 202 and 204, corresponding connectors 122 and 124 and corresponding stretchable loop extension elements 112 and 114 from being retracted into sclera 256.

As further shown in FIG. 21, forceps 290 are employed at a point distal to connector motion-limiting element 176 and at a point distal to extension element retaining element 182 to stretch stretchable loop extension element 112 and to thereby release loop 202 from connector 122. As described hereinabove, in the stretched configuration, the diameter of elongate stretchable loop extension element 112 is narrower than the diameter of cylindrical bore 152, thereby releasing elongate stretchable loop extension element 112 from inner surface 174 of cylindrical bore 152 and thereby allowing for release of loop 202 from connector 122. As further described hereinabove, once pulled through sclerectomy 274, connector 124 is operative to serve as a motion-limiting element which prevents loop 204, connector 124 and stretchable loop extension element 114 from being retracted into sclera 256 while releasing loop 202 from connector 122. After releasing loop 202 from connector 122, loop 202 is then fixated into a bore 296 formed in a side surface of recess 262.

Figure 22A:
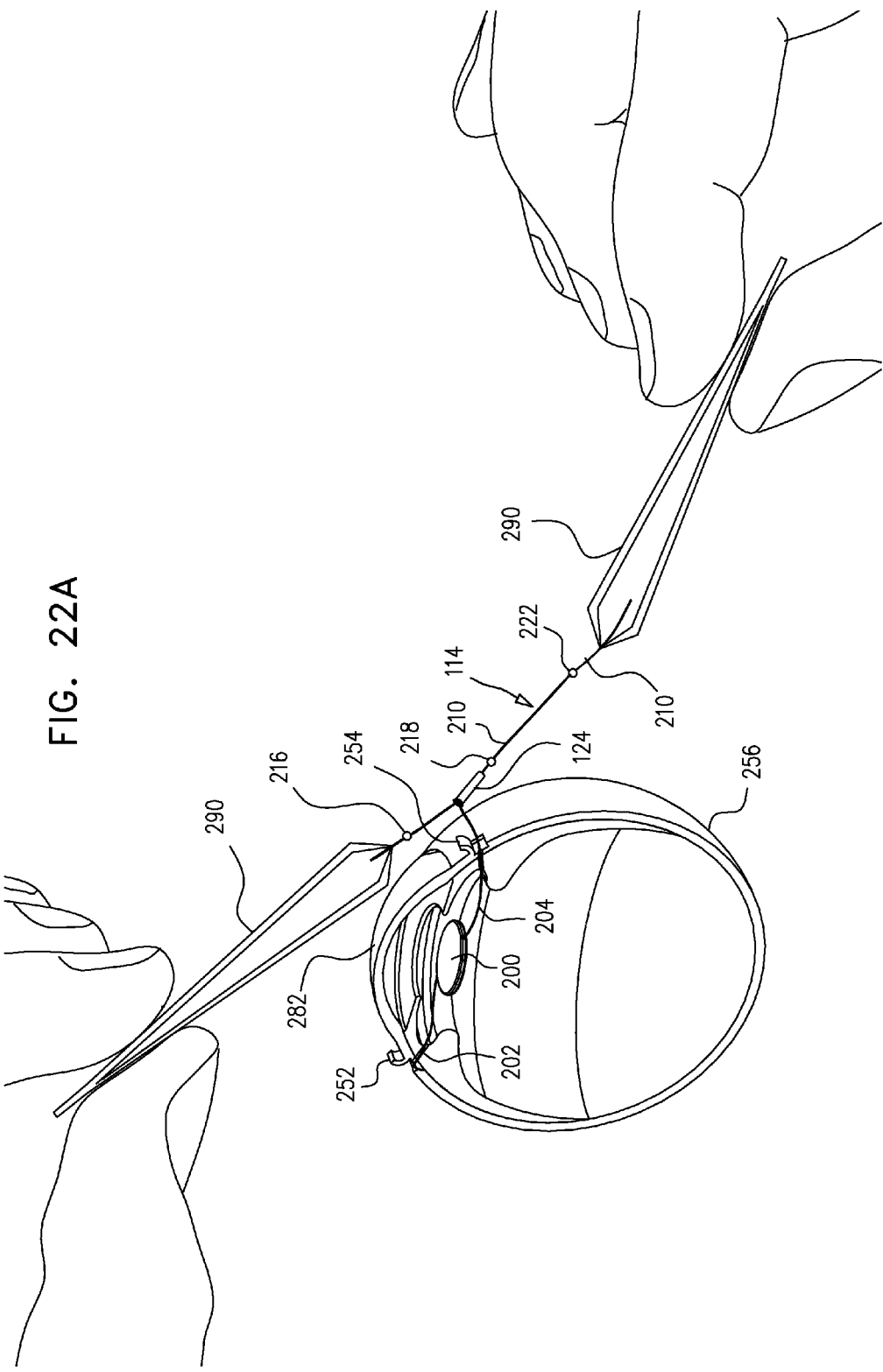

Similarly, as further shown in FIG. 22A, forceps 290 are employed at a point distal to connector motion-limiting element 216 and at a point distal to extension element retaining element 222 to stretch stretchable loop extension element 114 and to thereby release loop 204 from connector 124. As described hereinabove, in the stretched configuration, the diameter of elongate stretchable loop extension element 114 is narrower than the diameter of cylindrical bore 154, thereby releasing elongate stretchable loop extension element 114 from inner surface 214 of cylindrical bore 154 and thereby allowing for release of loop 204 from connector 124 and fixation of loop 204 into a bore 298 formed in a side surface of recess 264. Released elongate stretchable loop extension element 114 is shown in FIG. 22B.

As shown in FIG. 23, loops 202 and 204 remain protruding through respective sclerectomies 272 and 274 and fixated into bores 296 and 298 formed in side surfaces of corresponding recesses 262 and 264, as described hereinabove with regard to FIGS. 21 and 22B.

Figure 24:
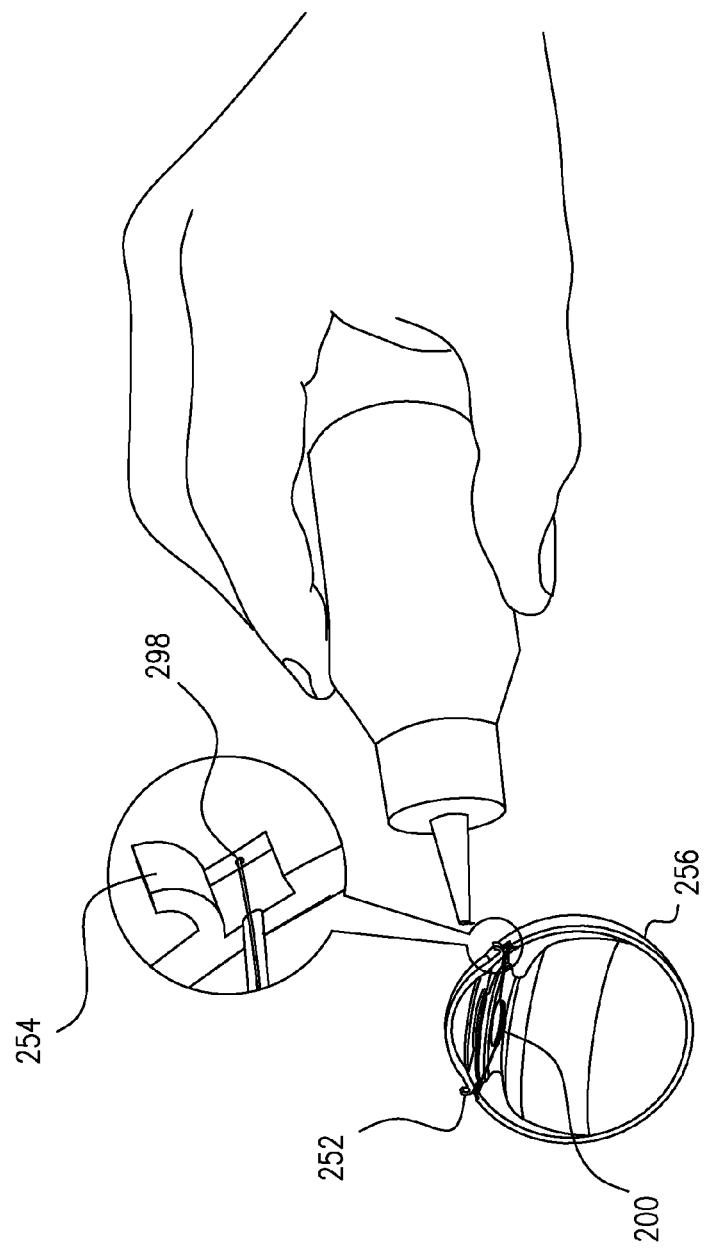
FIG. 24 is a simplified pictorial illustration of a seventh step in the implanting of an intraocular lens which is part of the intraocular lens assembly of FIG. 16 into an eye of a patient.

Turning now to FIG. 24, it is shown that after loose ends of loops 202 and 204 are inserted into corresponding bores 296 and 298, surgical glue is applied to a bottom surface of each of recesses 262 and 264. Thereafter, as shown in FIG. 25, scleral flaps 252 and 254 are folded back into respective recesses 262 and 264, thereby gluing flaps 252 and 254 into corresponding recesses 262 and 264 and thereby forming a smooth surface of sclera 256.

It will be appreciated by persons skilled in the art that the present invention is not limited by what has been particularly shown and described hereinabove. Rather the scope of the present invention includes both combinations and subcombinations of the various features described hereinabove as well as modifications thereof which would occur to persons skilled in the art upon reading the foregoing description and which are not in the prior art.

The invention claimed is:

1. A method for insertion of an intraocular lens into the eye of a patient, the method comprising:
   providing an intraocular lens assembly, said intraocular lens assembly including an intraocular lens with loops attached thererto and loop extensions removably attached to said loops of said intraocular lens;
   initially inserting into the eye of the patient said loop extensions of said intraocular lens assembly;
   pulling on said loop extensions through sclerectomies formed in the sclera of said eye of said patient;
   inserting said intraocular lens into said eye of said patient;
   positioning said intraocular lens in a desired position in said eye of said patient by pulling on said loop extensions through said sclerectomies;
   fixing said loops to said sclera of said eye of said patient at said sclerectomies; and
   detaching said loop extensions from said loops.

2. A method for insertion of an intraocular lens into the eye of a patient according to claim 1 and wherein each loop extension of said loop extensions comprises an elongate stretchable loop extension element formed of stretchable silicon, a thickness of said elongate stretchable loop extension element varying as a function of an extent to which said elongate stretchable loop extension element is stretched.

3. A method for insertion of an intraocular lens into the eye of a patient according to claim 2 and wherein each loop extension of said loop extensions also comprises a corresponding connector having a longitudinal cylindrical bore formed therewithin, said elongate stretchable loop extension element of said loop extension being threaded through said longitudinal cylindrical bore.

4. A method for insertion of an intraocular lens into the eye of a patient according to claim 3 and wherein each of said connectors comprises a cylindrical portion and a funnel shaped portion.

5. A method for insertion of an intraocular lens into the eye of a patient according to claim 3 and wherein each elongate stretchable loop extension element of each loop extension comprises a pair of connector motion-limiting elements integrally formed thereon for retaining said corresponding connector therebetween in a partially pretensioned configuration, a section of said elongate stretchable loop extension element being stretchably threaded within said corresponding connector, thereby retaining said connector motion-limiting elements in tight engagement with said corresponding connector.

6. A method for insertion of an intraocular lens into the eye of a patient according to claim 3 and wherein said pulling on said loop extensions through said sclerectomies formed in said sclera of said eye of said patient comprises pulling said elongate stretchable loop extension elements of said loop extensions, said corresponding connectors of said loop extensions and said corresponding loops of said intraocular lens from within said sclera through said sclerectomies.

7. A method for insertion of an intraocular lens into the eye of a patient according to claim 6 and wherein once pulled through said sclerectomies, each connector of said connectors is operative to serve as a motion-limiting element which prevents a corresponding one of said loops, said connector and a corresponding one of said elongate stretchable loop extension elements from being retracted into said sclera.

8. A method for preparation of an intraocular lens for insertion into an eye of a patient and insertion of the intraocular lens into the eye of the patient, the method comprising:
   providing an intraocular lens with loops attached thereto;
   removably attaching loop extensions to said loops of said intraocular lens prior to insertion of said intraocular lens into the eye of a patient;
   initially inserting into the eye of the patient said loop extensions;
   pulling on said loop extensions through sclerectomies formed in the sclera of said eye of said patient;
   inserting said intraocular lens into said eye of said patient;
   positioning said intraocular lens in a desired position in said eye of said patient by pulling on said loop extensions through said sclerectomies; and
   fixing said loops to said sclera of said eye of said patient at said sclerectomies; and
   detaching said loop extensions from said loops.

9. A method according to claim 8 and wherein each loop extension of said loop extensions comprises an elongate stretchable loop extension element formed of stretchable silicon, a thickness of said elongate stretchable loop extension element varying as a function of an extent to which said elongate stretchable loop extension element is stretched.

10. A method according to claim 9 and wherein each loop extension of said loop extensions also comprises a corresponding connector having a longitudinal cylindrical bore formed therewithin, said elongate stretchable loop extension element of said loop extension being threaded through said longitudinal cylindrical bore.

11. A method according to claim 10 and wherein each of said connectors comprises a cylindrical portion and a funnel shaped portion.

12. A method according to claim 10 and wherein each elongate stretchable loop extension element of each loop extension comprises a pair of connector motion-limiting elements integrally formed thereon for retaining said corresponding connector therebetween in a partially pretensioned configuration, a section of said elongate stretchable loop extension element being stretchably threaded within said corresponding connector, thereby retaining said connector motion-limiting elements in tight engagement with said corresponding connector.

13. A method according to claim 10 and wherein said removably attaching loop extensions to said loops of said intraocular lens comprises:
   stretching and retaining said elongate stretchable loop extension element of each of said loop extensions from an unstretched unfastened configuration to a retained stretched configuration;
   while said elongate stretchable loop extension element is in said retained stretched configuration, inserting an end of a corresponding one of said loops into said longitudinal cylindrical bore of said connector of said loop extension; and after inserting an end of a corresponding one of said loops into said longitudinal cylindrical bore of said connector of said loop extension, releasing said elongate stretchable loop extension element from said retained stretched configuration, thereby placing said elongate stretchable loop extension element in an unstretched fastened configuration.

14. A method according to claim 13 and wherein when said elongate stretchable loop extension element is in said unstretched unfastened configuration, a diameter of said elongate stretchable loop extension element is generally equal to a diameter of said longitudinal cylindrical bores of said corresponding connector, thereby tightly engaging said elongate stretchable loop extension element with an inner surface of said longitudinal cylindrical bore of said corresponding connector, and thereby tightly retaining said corresponding connector in a fixed position on said elongate stretchable loop extension element.

15. A method according to claim 13 and wherein when said elongate stretchable loop extension element is in said retained stretched configuration, a diameter of said elongate stretchable loop extension element is narrower than a diameter of said longitudinal cylindrical bore, thereby releasing said elongate stretchable loop extension element from an inner surface of said longitudinal cylindrical bore of said corresponding connector.

16. A method according to claim 15 and wherein said elongate stretchable loop extension element comprises a pair of connector motion-limiting elements integrally formed thereon for retaining said corresponding connector therebetween when said elongate stretchable loop extension element is in said retained stretched configuration.

17. A method according to claim 13 and wherein when said elongate stretchable loop extension element is in said unstretched fastened configuration, a diameter of said elongate stretchable loop extension element is generally equal to a diameter of said longitudinal cylindrical bore of said corresponding connector, thereby tightly engaging said elongate stretchable loop extension element and said loop with an inner surface of said cylindrical bore of said longitudinal cylindrical bore of said corresponding connector, and thereby fastening said loop to said elongate stretchable loop extension element.

18. A method according to claim 13 and wherein said detaching said loop extension from said loop comprises:
stretching said elongate stretchable loop extension element of said loop extension from said unstretched fastened configuration to a stretched unfastened configuration; and
releasing said loop from said connector.

19. A method according to claim 18 and wherein when elongate stretchable loop extension element is in said stretched unfastened configuration, a diameter of said elongate stretchable loop extension element is narrower than a diameter of said longitudinal cylindrical bore of said corresponding connector, thereby releasing said elongate stretchable loop extension element and said loop from an inner surface of said longitudinal cylindrical bore of said corresponding connector.

20. A method according to claim 10 and wherein said pulling on said loop extensions through said sclerectomies formed in said sclera of said eye of said patient comprises pulling said elongate stretchable loop extension elements of said loop extensions, said corresponding connectors of said loop extensions and said corresponding loops of said intraocular lens from within said sclera through said sclerectomies.

21. A method according to claim 20 and wherein once pulled through said sclerectomies, each connector of said connectors is operative to serve as a motion-limiting element which prevents a corresponding one of said loops, said connector and a corresponding one of said elongate stretchable loop extension elements from being retracted into said sclera.

* * * * *